US008207110B2

(12) United States Patent
Suciu-Foca et al.

(10) Patent No.: US 8,207,110 B2
(45) Date of Patent: Jun. 26, 2012

(54) ITL3 POLYPEPTIDES AND USES THEREOF

(75) Inventors: Nicole Suciu-Foca, New York, NY (US); Luigi Scotto, Stamford, CT (US); Seunghee Kim-Schulze, Tenafly, NJ (US); George Vlad, Forest Hills, NY (US); Raffaello Cortesini, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 854 days.

(21) Appl. No.: 11/661,877

(22) PCT Filed: Sep. 1, 2005

(86) PCT No.: PCT/US2005/031380
§ 371 (c)(1),
(2), (4) Date: Jul. 1, 2008

(87) PCT Pub. No.: WO2006/033811
PCT Pub. Date: Mar. 30, 2006

(65) Prior Publication Data
US 2008/0311073 A1 Dec. 18, 2008

Related U.S. Application Data

(60) Provisional application No. 60/607,095, filed on Sep. 3, 2004, provisional application No. 60/622,165, filed on Oct. 26, 2004.

(51) Int. Cl.
*A61K 38/00* (2006.01)
(52) U.S. Cl. ..................................... 514/1.1
(58) Field of Classification Search .................. None
See application file for complete search history.

(56) References Cited

U.S. PATENT DOCUMENTS

| | | | |
|---|---|---|---|
| 4,515,895 | A | 5/1985 | Kung et al. |
| 4,652,447 | A | 3/1987 | Kung et al. |
| 4,658,020 | A | 4/1987 | Kung et al. |
| 4,677,056 | A | 6/1987 | Dupont et al. |
| 4,816,404 | A | 3/1989 | Suciu-Foca et al. |
| 4,818,689 | A | 4/1989 | Suciu-Foca et al. |
| 5,156,951 | A | 10/1992 | Bach et al. |
| 6,384,203 | B1 | 5/2002 | Anderson et al. |
| 6,759,239 | B2 | 7/2004 | Suciu-Foca et al. |
| 7,144,728 | B1 | 12/2006 | Suciu-Foca et al. |
| 2003/0118997 | A1 | 6/2003 | Bejanin et al. |
| 2003/0165875 | A1 | 9/2003 | Colonna et al. |
| 2004/0241167 | A1 | 12/2004 | Suciu-Foca et al. |

FOREIGN PATENT DOCUMENTS

| | | |
|---|---|---|
| WO | WO98/48017 | 10/1998 |
| WO | WO 98/48017 | 10/1998 |
| WO | WO 00/68383 | 11/2000 |
| WO | WO2006/033811 | 3/2006 |

OTHER PUBLICATIONS

Whisstock et al., 2003 Quart. Rev. Biophys. vol. 36: 307-340.*
Wang et al., 2001, J. Biol. Chem. vol. 276, 49213-20.*
Zotova et al., 2010, Alz. Res. vol. 2: 1-9.*
Exper Opin Ther. Patents, 2008, vol. 18: 555-561.*
Chang et al., "Tolerization of dendritic cells by Ts cells: the crucial role of inhibitory receptors ILT3 and ILT4," *Nature Immunology*, 3:237-243 (2002).
Manavalan et al., "High expressionof ILT3 and ILT4 is a general feature of tolerogenic dendritic cells," *Transplant Immunology*, 11:245-258 (2003).
Suciu-Foca et al., "Soluble Ig-like transcript 3 inhibits tumor allograft rejection in humanized SCID Mice and T cell responses in cancer patient," *Journal of Immunology*, 178:7432-7441 (2007).
Suciu-Foca et al., "Central role of ILT3 in the T suppressor cell cascade," *Cellular Immunology*, 248:59-67 (2007).
Banchereau et al., "Immunbiology of dendritic cells," *Annu. Rev. Immunol.*, 18:767-811 (2000).
Cella et al., "A novel inhibitory receptor (ILT3) expressed on monocytes, macrophages, and dendritic cells involved in antigen processing," *J. Exp. Med.*, 185:1743-1751 (1997).
Ciubotariu et al., "Detection of T suppressor cells in patients with organ allografts," *Hum. Immunol..* 62:15-20 (2001).
Ciubotariu et al., "Specific suppression of human CD4+ Th cell responses to pig MHC antigens by CD8+ CD28 regulatory T cells," *J. Immunol.*, 161:5193-5202 (1998).
Ciubotariu et al, "Persistent allopeptide reactivity and epitope spreading in chronic rejection of organ allografts," *J. Clin. Invest.*, 101:398-405 (1998).
Colonna et al., "A family of inhibitory and activating Ig-like receptors that modulate function of lymphoid and myeloid cells," *Semin. Immunol.*, 12:121-127 (2000).
Colonna et al., "A novel family of Ig-like receptors for HLA class I molecules that modulate function of lymphoid and myeloid cells," *J. Leukoc. Biol.*, 66:375-381 (1999).
Colonna et al., "Cutting edge: human myelomonocytic cells express an inhibitory receptor for classical and nonclassical MHC class I molecules," *J. Immunol.*, 160:3096-3100 (1998).
Colovai et al., "Induction of xenoreactive CD4+ T-cell anergy by suppressor CD8+ CD28− T cells," *Transplantation*, 69:1304-1310 (2000).
Cotner et al., "Simultaneous flow cytometric analysis of human T cell activation antigen expression and DNA content," *J. Exp. Med.*, 157:461472 (1983).

(Continued)

*Primary Examiner* — Amy Juedes
(74) *Attorney, Agent, or Firm* — Evans & Molinelli PLLC; Judith A. Evans

(57) ABSTRACT

This invention provides a first polypeptide comprising all or a portion of the extracellular domain of ILT3, wherein the polypeptide is water-soluble and does not comprise the Fc portion of an immunoglobulin. This invention also provides a second polypeptide comprising (i) all or a portion of the extracellular domain of ILT3 operable affixed to (ii) the Fc portion of an immunoglobulin, wherein the Fc portion of the immunoglobulin comprises a function-enhancing mutation, and wherein the polypeptide is water-soluble. This invention further provides a third polypeptide comprising (i) all or a portion of the extracellular domain of ILT3 operable affixed to (ii) a transmembrane domain. This invention further provides related nucleic acids, expression vectors, host vector systems, compositions, and articles of manufacture and therapeutic and prophylactic methods using the polypeptides of the invention.

4 Claims, 20 Drawing Sheets

OTHER PUBLICATIONS

Damle et al., "Alloantigen-specific cytotoxic and suppressor T lymphocytes are derived from phenotypically distinct precursors," *J. Immunol.*,131:2296-2300 (1983).

Dhodapkar et al., "Antigen-specific inhibition of effector T cell function in humans after injection of immature dendritic cells," *J. Exp. Med.*, 93:233-238 (2001).

Garcia-Alonso et al., "CD28 expression on peripheral blood T lymphocytes after orthotopic liver transplant: upregulation in acute rejection," *Hum. Immunol.*, 53:64-72 (1997).

Groux et al., "A CD4 + T-cell subset inhibits antigen-specific T-cell responses and prevents colitis," *Nature*, 89:737-742 (1997).

Haars et al., "Modulation of T-cell antigen receptor on lymphocyte membrane," *Immunogenetics*, 20:397-405 (1984).

Jenkins et al., "Antigen presentation by chemically modified splenocytes induces antigen-specific T cell unresponsiveness in vitro and in vivo," *J. Exp. Med.*,165:302-319 (1987).

Jiang et al., "Induction of MHC-class I restricted human suppressor T cells by peptide priming in vitro," *Hum. Immunol.*, 59:690-699 (1998).

Jonuleit et al., "Identification and functional characterization of human CD4(+)CD25(+) T cells with regulatory properties isolated from peripheral blood," *J. Exp. Med.*, 193:1285-1294 (2001).

Jonuleit et al., "Induction of interleukin 10-producing, nonproliferating CD4(+) T cells with regulatory properties by repetitive stimulation with allogeneic immature human dendritic celis," *J. Exp. Med.*,192:1213-1222 (2000).

Lanzavecchia, "Immunology. License to kill," *Nature*, 393:413-414 (1998).

Lechler et al., "Dendritic cells in transplantation—friend or foe?," *Immunity*, 14:357-368 (2001).

Li et al., "T suppressor lymphocytes inhibit NFKB-mediated transcription of CD86 gene in APC," *J. Immunol.*, 163:6386-6392 (1999).

Liu et al., "Inhibition of CD40 signaling pathway in antigen presenting cells by T suppressor cells," *Hum. Immunol.*, 60:568-574 (1999).

Liu et al., "Specific suppression of T helper alloreactivity by allo-MHC class I-restricted CD8+ CD28– T cells," *Int. Immunol.*, 10:775-783 (1998).

Lutz et al., "Immature dendritic cells generated with low doses of GM-CSF in the absence of IL-4 are maturation resistant and prolong allograft survival in vivo," *Eur. J. Immunol.*, 30:1813-1822 (2000).

Mingari et al., "Regulation of KIR expression in human T cells: A safety mechanism that may impair protective T-cell responses," *Immunol. Today*, 19:153-157 (1998).

Mingari et al., "Human CD8+ T lymphocyte subsets that express HLA class I-specific inhibitory receptors represent oligoclonally or monoclonally expanded cell populations," PNAS, 93:12433-12438 (1996).

Ravetch et al., "Immune inhibitory receptors," *Science*, 290:84-88 (2000).

Rea et al., "Glucocorticoids transform CD40-triggering of dendritic cells into an alternative activation pathway resulting in antigen-presenting cells that secrete IL-10," *Blood*, 95:3162-3167 (2000).

Roncarolo et al., "Differentiation of T regulatory cells by immature dendritic cells," *J. Exp. Med.*, 193:F5-F9 (2001).

Sakaguchi, "Regulatory T cells: Key controllers of immunologic self-tolerance," *Cell*, 101, 455-458 (2000).

Schwartz, "Models of T cell anergy: is there a common molecular mechanism?," *J. Exp. Med.*,184:1-8 (1996).

Shevach, "Regulatory T cells in autoimmunity," *Annu. Rev. Immunol.*,18:423-449 (2000).

Steinman et al., "The induction of tolerance by dendritic cells that have captured apoptotic cells," *J. Exp. Med.*, 191 :411-416 (2000).

Steinman, "The dendritid cell system and its role in immunogenicity," *Annu. Rev. Immunol.*,9:271-296 (1991).

Suciu-Foca Cortesini et al., "Distinct mRNA microarray profiles of tolerogenic dendritic cells," *Hum. Immunol.*,62:1065-1072 (2001).

Suciu-Foca Cortesini et al., "A late-differentiation antigen associated with the helper inducer function of human T cells," *Nature*, 318:465-467 (1985).

Suciu-Foca Cortesini et al., "Idiotypic network regulations of the immune response to HLA," *Transplantation Proceedings*, 17(1):716-719 (1985).

Takahashi et al., "Immunologic self-tolerance maintained by CD25+ CD4+ regulatory T cells constitutively expressing cytotoxic T lymphocyte-associated antigen 4," *J. Exp. Med.*, 192:303-310 (2000).

Beinhauer et al., 2004, Interleukin 10 regulates cell surface and soluble LIR-2 (CD885d) expression on dendritic cells resulting in T cell hyporesponsiveness in vitro, Eur. J. Immunol. 34:74-80.

Kim-Schulze et al., 2006, Recombinant Ig-Like Transcript 3-Fc Modulates T Cell Responses via Induction of Th Anergy and Differentiation of CD8+ T Suppressor Cells, J. Immunology 176:2790-2798.

Leukocyte Immunoglobulin-like Receptor, Subfamily B. Member 4; LILRB4, OMIM 604821 (2000).

* cited by examiner

ITL3 POLYPEPTIDES AND USES THEREOF

CROSS-REFERENCE TO RELATED APPLICATIONS

This application is a United States National Phase of International Application PCT/US2005/031380 filed Sep. 1, 2005, which application claims priority and benefit from United States Provisional Applications 60/622,165, filed Oct. 26, 2004, and 60/607,095, filed Sep. 3, 2004. The contents of the prior PCT application and US provisional applications are incorporated herein by reference in their entirety.

The instant application contains a Sequence Listing which has been submitted via EFS-Web and is hereby incorporated by reference in its entirety. The ASCII text file, named sequence.txt, is 844 bytes in size and was created on Mar. 13, 2009.

Throughout this invention, various publications are referenced. Full citations for these publications are presented immediately before the claims. Disclosures of these publications in their entireties are hereby incorporated by reference into this application in order to more fully describe the state of the art to which this invention pertains.

The invention disclosed herein was made with government support from the National Institutes of Health under grant nos. AI2521-18 and AI55234-02. Accordingly, the U.S. Government has certain rights in this invention.

BACKGROUND OF THE INVENTION

LIRs

Leukocyte Ig-like receptors ("LIRs,") are a family of immunoreceptors expressed predominantly on monocytes and B cells and at lower levels on dendritic cells and natural killer ("NK") cells. Activation of various immune cell types can be prevented by negative signaling receptors through interactions with specific ligands, such as MHC class I molecules by NK cells. All of the LIR inhibitory receptors, members of subfamily B, contain a cytoplasmic immunoreceptor tyrosine-based inhibitory motif ("ITIM"). Upon MHC class I (or other ligand) engagement and tyrosine phosphorylation of the ITIM, intracellular protein-tyrosine phosphatases such as SHP1 are recruited, and an inhibitory signal cascade ensues. Other LIR receptors, members of subfamily A, with short cytoplasmic regions containing no ITIMs and with transmembrane regions containing a charged arginine residue, may initiate stimulatory cascades. One member of subfamily A lacks a transmembrane region and is presumed to be a soluble receptor (1). LIR-5, one type of LIR, is also known as ILT3.

ILT3 Fusion Proteins

A soluble fusion protein made of a soluble portion of ILT3 and the Fc portion of IgG1 is known. However, this fusion protein was used merely as a negative control in an endotoxemia study, and its potential use as a therapeutic was not disclosed (2).

Soluble ILT4

LIR-2, also known as ILT4, is an inhibitory receptor. However, its soluble form was shown to completely restore the proliferation of T-cells activated with LPS and IL-10-treated dendritic cells (3).

SUMMARY OF THE INVENTION

This invention provides a first polypeptide comprising all or a portion of the extracellular domain of ILT3, wherein the polypeptide is water-soluble and does not comprise the Fc portion of an immunoglobulin.

This invention also provides a second polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble.

This invention further provides a third polypeptide comprising (i) all or a portion of the extracellular domain of ILT3 operably affixed to (ii) a transmembrane domain. In one embodiment the transmembrane domain corresponds to or is derived from the transmembrane domain of human ILT3 (e.g., amino acid residues 259 to 280 of the sequence of GenBank Accession No. U82979). In another embodiment, the transmembrane domain is derived from a protein other than human ILT3 wherein the protein comprises a transmembrane domain. Nucleic acids encoding these polypeptides, expression vectors comprising the nucleic acids and host cells comprising the nucleic acids or vectors are provided. Methods for producing these polypeptides (e.g., by culturing a host cell comprising a nucleic acid encoding the polypeptide or vector comprising the nucleic acid under conditions that allow expression of the encoded polypeptide and recovering the polypeptide are also provided.

This invention provides a first isolated nucleic acid which encodes a polypeptide comprising all or a portion of the extracellular domain of ILT3, wherein the polypeptide is water-soluble and does not comprise the Fc portion of an immunoglobulin.

This invention further provides a second isolated nucleic acid which encodes a polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble.

This invention provides a first expression vector comprising a nucleic acid sequence encoding a polypeptide comprising all or a portion of the extracellular domain of ILT3, wherein the polypeptide is water-soluble and does not comprise the Fc portion of an immunoglobulin.

This invention further provides a second expression vector comprising a nucleic acid sequence encoding a polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble.

This invention provides a first host vector system which comprises the first expression vector and a suitable host cell.

This invention further provides a second host vector system which comprises the second expression vector and a suitable host cell.

This invention provides a method for producing the first polypeptide, comprising (a) culturing the first host vector system under conditions permitting polypeptide synthesis by the host vector system, and (b) recovering the polypeptide so produced.

This invention also provides a method for producing the second polypeptide, comprising (a) culturing the second host vector system under conditions permitting polypeptide synthesis by the host vector system, and (b) recovering the polypeptide so produced.

This invention provides a first composition comprising (a) a pharmaceutically acceptable carrier and (b) the first polypeptide.

This invention further provides a second composition comprising (a) a pharmaceutically acceptable carrier and (b) the second polypeptide.

This invention also provides a third composition comprising (a) a pharmaceutically acceptable carrier and (b) the third polypeptide.

This invention provides a method for inhibiting the onset of transplant rejection in a subject who has received, or is about to receive, a transplant, comprising administering to the subject a prophylactically effective amount of the first, second or third polypeptide.

This invention further provides a method for treating transplant rejection in a subject who has received a transplant, comprising administering to the subject a therapeutically effective amount of the first, second or third polypeptide. Also contemplated are methods of preventing or treating graft versus host disease by administering the polypeptides of this invention to a subject in need thereof.

This invention provides a method for treating a subject afflicted with an autoimmune disorder, comprising administering to the subject a therapeutically effective amount of the first, second or third polypeptide.

This invention further provides a method for treating a subject afflicted with an inflammatory disorder, comprising administering to the subject a therapeutically effective amount of the first, second or third polypeptide.

This invention further provides a method for inducing anergy in a T cell, thereby causing it to differentiate into a regulatory cell, comprising contacting the T cell with the first, second or third polypeptide under conditions permitting priming of the T cell to occur, thereby inducing anergy in the T cell and causing it to differentiate into a regulatory cell.

This invention further comprises a method for treating a subject afflicted with an autoimmune disorder, comprising (a) contacting, ex vivo, the first, second or third polypeptide with T cells obtained from the subject, wherein the contacting is performed under conditions permitting priming of the cells to occur, and (b) intravenously administering the resulting cells to the subject, so as to treat the subject.

This invention further provides an article of manufacture comprising (a) a packaging material having therein the first polypeptide, and (b) a label indicating a use for the polypeptide for (i) treating or inhibiting the onset of transplant rejection in a subject, (ii) treating an autoimmune disorder in a subject, or (iii) treating an inflammatory disorder in a subject.

Finally, this invention provides an article of manufacture comprising (a) a packaging material having therein the second polypeptide, and (b) a label indicating a use for the polypeptide for (i) treating or inhibiting the onset of transplant rejection in a subject, (ii) treating an autoimmune disorder in a subject, or (iii) treating an inflammatory disorder in a subject.

DETAILED DESCRIPTION OF THE INVENTION

Figure 1:
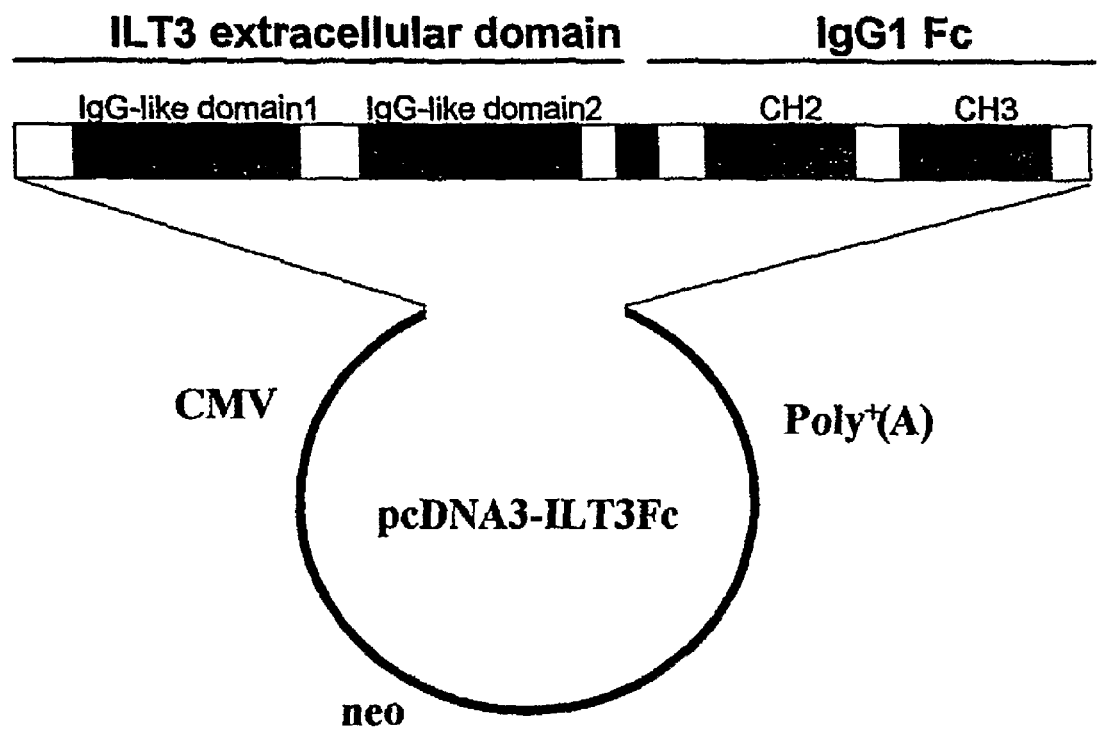
FIG. 1
Schematic drawing of soluble ILT3 expression vector.
Figure 2:
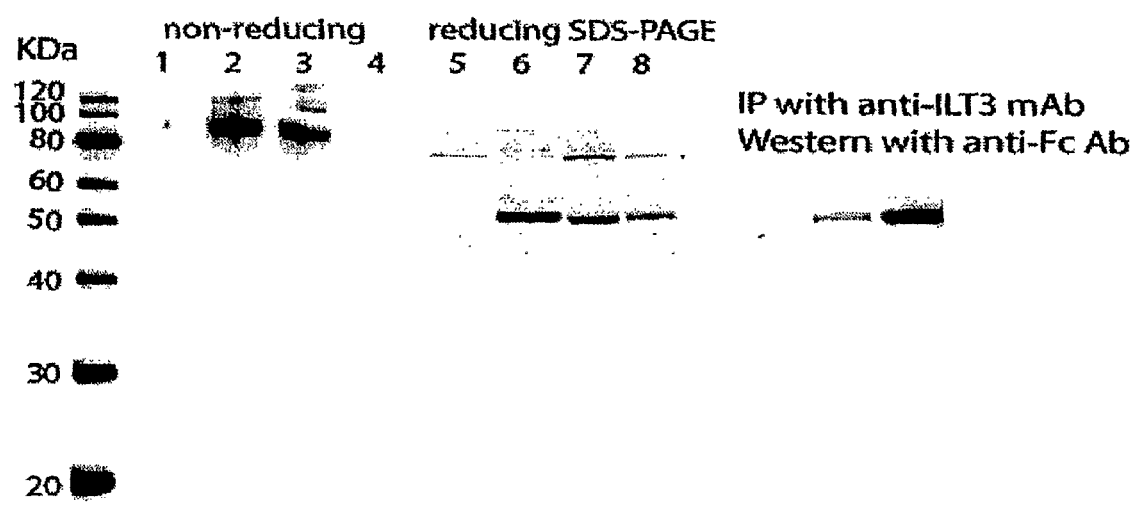
FIG. 2
Western Blot analysis of soluble ILT3 fusion protein.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Principles of Neural Science, 4$^{th}$ ed., Eric R. Kandel, James H. Schwart, Thomas M. Jessell editors. McGraw-Hill/Appleton & Lange: New York, N.Y. (2000). The nomenclatures used in connection with, and the laboratory procedures and techniques of, molecular and cellular neurobiology and medicinal and pharmaceutical chemistry described herein are those well known and commonly used in the art. Standard techniques are used for chemical syntheses, chemical analyses, pharmaceutical preparation, formulation, and delivery, and treatment of patients.

Throughout this specification, the word "comprise" or variations such as "comprises" or "comprising" will be understood to imply the inclusion of a stated integer or group of integers but not the exclusion of any other integer or group of integers.

Definitions

"Administering" shall mean delivering in a manner which is effected or performed using any of the various methods and delivery systems known to those skilled in the art. Administering can be performed, for example, topically, intravenously, pericardially, orally, via implant, transmucosally, transdermally, intramuscularly, subcutaneously, intraperitoneally, intrathecally, intralymphatically, intralesionally, or epidurally. Administering can also be performed, for example, once, a plurality of times, and/or over one or more extended periods.

"Agent" shall include, without limitation, an organic or inorganic compound, a nucleic acid, a polypeptide, a lipid, a carbohydrate or a physical stimulus. Agents include, for example, agents which are known with respect to structure and/or function, and those which are not known with respect to structure or function.

"Concurrent" administration of two agents shall mean administration wherein the time period over which the first agent is administered either overlaps with, or is coincident with, the time period over which the second agent is administered. For example, a first and a second agent are concurrently administered if the first agent is administered once per week for four weeks, and the second agent is administered twice per week for the first three of those four weeks. Likewise, for example, a first and second agent are concurrently administered if the first and second agent are each administered, in the same or separate pills, on the same day, once per week for four weeks.

"Expression vector" shall mean a nucleic acid encoding a nucleic acid of interest and/or a protein of interest, which nucleic acid, when placed in a cell, permits the expression of the nucleic acid or protein of interest. Expression vectors are well known in the art.

"Extracellular domain of ILT3" shall mean the N-terminal 258 amino acid residues of ILT3 (e.g., human ILT3 having the sequence of GenBank Accession No. U82979). A "portion" of the extracellular domain of ILT3 includes, for example, the IgG1-like domain 1 (residues 42-102 of human ILT3), the IgG1-like domain 2 (residues 137-197 of human ILT3), and the N-terminal 250, 240, 230, 220, 210, 200, 190, 180, 170, 160 or 150 amino acid residues of ILT3.

"Function-enhancing mutation", with respect to the second polypeptide of this invention, shall mean any mutation which confers a physical property (e.g., reduced binding of the Fc moiety to an Fc receptor) to the polypeptide which permits it to better accomplish its therapeutic role (e.g., through increasing its half-life or reducing adverse effects otherwise caused by a subject's immune system).

"ILT3" shall mean "Immunoglobulin-Like Transcript-3", and is synonymous with "ILT-3", "LIR-5", "CD85K" and "LILRB4." The mRNA coding sequence for human ILT3 is provided under GenBank No. U82979.

"Immunoglobulin" and "antibody" are used synonymously herein, and shall include, by way of example, both naturally occurring and non-naturally occurring antibodies. Specifically, this term includes polyclonal and monoclonal antibodies, and antigen-binding fragments (e.g., Fab fragments, as opposed to Fc fragments) thereof. Furthermore, this term includes chimeric antibodies (e.g., humanized antibodies) and wholly synthetic antibodies, and antigen-binding fragments thereof. Within the scope of the term "antibody" are also antibodies that have been modified in sequence, but remain capable of specific binding to an antigen. Example of modified antibodies are interspecies chimeric and humanized antibodies; antibody fusions; and heteromeric antibody complexes, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513), the disclosure of which is incorporated herein by reference in its entirety).

"Inhibiting" the onset of a disorder shall mean either lessening the likelihood of the disorder's onset, or preventing the onset of the disorder entirely. In the preferred embodiment, inhibiting the onset of a disorder means preventing its onset entirely.

"Mammalian cell" shall mean any mammalian cell. Mammalian cells include, without limitation, cells which are normal, abnormal and transformed, and are exemplified by neurons, epithelial cells, muscle cells, blood cells, immune cells, stem cells, osteocytes, endothelial cells and blast cells.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Operably affixed", with respect to the second polypeptide of this invention, shall mean affixed (e.g., via peptide bond) in a manner permitting the ILT3 moiety thereof to inhibit the proliferation of CD4$^+$ T cells. In one embodiment, a polypeptide linker of 10, 11, 12, 13, 14, 15 or 16 amino acid residues in length is used to join the ILT3 and Fc moieties.

"Pharmaceutically acceptable carriers" are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Porphyrin or Lipofectin may also be used as a delivery agent. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

"Polypeptide" and "protein" are used interchangeably herein, and each means a polymer of amino acid residues. The amino acid residues can be naturally occurring or chemical analogues thereof. Polypeptides and proteins can also include modifications such as glycosylation, lipid attachment, sulfation, hydroxylation, and ADP-ribosylation. A variety of methods for labeling polypeptides and substituents or labels useful for such purposes are well known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., 1992, hereby incorporated by reference.

"Prophylactically effective amount" means an amount sufficient to inhibit the onset of a disorder or a complication associated with a disorder in a subject.

"Subject" shall mean any organism including, without limitation, a mammal such as a mouse, a rat, a dog, a guinea pig, a ferret, a rabbit and a primate. In the preferred embodiment, the subject is a human being.

"Therapeutically effective amount" means any amount of an agent which, when administered to a subject afflicted with a disorder against which the agent is effective, causes the subject to be treated.

"Transplant rejection" shall mean the adverse response by the immune system of a subject who has received a transplant (e.g., of an organ or tissue). Transplanted organs in this context include, for example, heart, kidney, skin, lung, liver, eye and bone. Transplanted tissue in this context includes, for example, vascular tissue.

"Treating" a subject afflicted with a disorder shall mean causing the subject to experience a reduction, remission or regression of the disorder and/or its symptoms. In one embodiment, recurrence of the disorder and/or its symptoms is prevented. In the preferred embodiment, the subject is cured of the disorder and/or its symptoms.

This invention provides a first polypeptide comprising all or a portion of the extracellular domain of ILT3, wherein the polypeptide is water-soluble and does not comprise the Fc portion of an immunoglobulin.

In one embodiment, the polypeptide is isolated. In a further embodiment, the polypeptide comprises the extracellular domain of ILT3. In yet a further embodiment, the polypeptide consists of the extracellular domain of ILT3. Preferably, the ILT3 is human ILT3. In one embodiment, the portion of ILT3 is the IgG1-like domain 1, the IgG1-like domain 2 or the N-terminal 250, 240, 230, 220, 210, 200, 190, 180, 170, 160 or 150 amino acid residues of ILT3. In another embodiment, the portion of the ILT3 is capable of inhibiting T cell proliferation or inducing differentiation of a T cell into a regulatory T cell. Assays to detect T cell proliferation and differentiation into regulatory T cells are well known in the art and include those described below. Such polypeptides are useful for preventing, inhibiting, reducing or suppressing immune responses mediated by the activation of T cells.

Also contemplated are polypeptides of the invention which contain minor variations provided that the variations in the amino acid sequence maintain at least 75%, more preferably at least 80%, 90%, 95%, and most preferably 99% sequence identity and the molecule retains bioactivity (e.g., inhibition of T cell proliferation, differentiation of T cells into regulatory T cells, suppression of immune responses mediated by activated T cells). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family.

This invention also provides a second polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble. The Fc portion may also be substituted with any other peptide that promotes dimerization or oligomerization. For example, the peptide may comprise cysteine residues that form disulfide bonds or other residues that promote covalent or nonconvalent interactions between the peptides such that the peptides mediate dimerization or oligomerization. Suitable peptides include leucine zippers (e.g., those derived from the yeast GCN4 or a modified version thereof. Other exemplary oligomerization domains are described in, e.g., WO 00/69907, WO 99/62953, WO 98/56906, WO 98/18943, and WO 96/37621.

In one embodiment, the polypeptide is isolated. In a further embodiment, the polypeptide comprises the extracellular domain of ILT3. Preferably, the ILT3 is human ILT3. In a further embodiment, the Fc portion of the immunoglobulin is the Fc portion of IgG1. Preferably, the IgG1 is human IgG1. In a further embodiment, the function-enhancing mutation in the Fc portion of the immunoglobulin inhibits the binding of the Fc portion of an immunoglobulin to an Fc receptor. In one example, the function-enhancing mutation in the Fc portion of the immunoglobulin is an Asn-->Gln point mutation at amino acid residue 77 of the Fc portion of human IgG1.

This invention further provides a third polypeptide comprising (i) all or a portion of the extracellular domain of ILT3 operably affixed to (ii) a transmembrane domain. In one embodiment the transmembrane domain corresponds to or is derived from the transmembrane domain of human ILT3 (e.g., amino acid residues 259 to 280 of the sequence of GenBank Accession No. U82979). In another embodiment, the transmembrane domain is derived from a protein other than human ILT3 wherein the protein comprises a transmembrane domain. Nucleic acids encoding these polypeptides, expression vectors and host cells comprising the nucleic acids and methods for producing these polypeptides are also provided.

Also contemplated are polypeptides of the invention which contain minor variations provided that the variations in the amino acid sequence maintain at least 75%, more preferably at least 80%, 90%, 95%, and most preferably 99% sequence identity and the molecule retains bioactivity (e.g., inhibition of T cell proliferation, differentiation of T cells into regulatory T cells, suppression of immune responses mediated by activated T cells). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family.

This invention provides a first isolated nucleic acid which encodes a polypeptide comprising all or a portion of the extracellular domain of ILT3, wherein the polypeptide is water-soluble and does not comprise the Fc portion of an immunoglobulin. This invention includes nucleic acids encoding polypeptides of the invention containing a conservative mutation as described above.

This invention further provides a second isolated nucleic acid which encodes a polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble.

In one embodiment of the instant nucleic acids, the nucleic acids are DNA (e.g., cDNA). In a further embodiment, the nucleic acids are RNA.

This invention provides a first expression vector comprising a nucleic acid sequence encoding a polypeptide comprising all or a portion of the extracellular domain of ILT3, wherein the polypeptide is water-soluble and does not comprise the Fc portion of an immunoglobulin.

This invention further provides a second expression vector comprising a nucleic acid sequence encoding a polypeptide comprising (i) all or a portion of the extracellular domain of ILT3 operably affixed to (ii) the Fc portion of an immunoglobulin, wherein the Fc portion of the immunoglobulin comprises a function-enhancing mutation, and wherein the polypeptide is water-soluble.

This invention provides a first host vector system which comprises the first expression vector and a suitable host cell.

This invention further provides a second host vector system which comprises the second expression vector and a suitable host cell.

The polypeptides of the invention may be expressed using any suitable vector. Typically, the vectors are derived from virus, plasmid, prokaryotic or eukaryotic chromosomal elements, or some combination thereof, and may optionally include at least one origin of replication, at least one site for insertion of heterologous nucleic acid, and at least one selectable marker. The invention also contemplates expressing the polypeptides of the invention using artificial chromosomes, e.g., bacterial artificial chromosomes (BACs), yeast artificial chromosomes (YACs), mammalian artificial chromosomes (MACs), and human artificial chromosomes (HACs), e.g., when it is necessary to propagate nucleic acids larger than can readily be accommodated in viral or plasmid vectors.

The vectors will also often include elements that permit in vitro transcription of RNA from the inserted heterologous nucleic acid. Such vectors typically include a phage promoter, such as that from T7, T3, or SP6, flanking the nucleic acid insert. Expression vectors often include a variety of other genetic elements operatively linked to the protein-encoding heterologous nucleic acid insert, typically genetic elements that drive and regulate transcription, such as promoters and enhancer elements, those that facilitate RNA processing, such as transcription termination, splicing signals and/or polyadenylation signals, and those that facilitate translation, such as ribosomal consensus sequences. Other transcription control sequences include, e.g., operators, silencers, and the like. Use of such expression control elements, including those that confer constitutive or inducible expression, and developmental or tissue-regulated expression are well-known in the art.

Expression vectors can be designed to fuse the expressed polypeptide to small protein tags that facilitate purification and/or visualization. Many such tags are known and available. Expression vectors can also be designed to fuse proteins encoded by the heterologous nucleic acid insert to polypeptides larger than purification and/or identification tags. Useful protein fusions include those that permit display of the encoded protein on the surface of a phage or cell, fusions to intrinsically fluorescent proteins, such as luciferase or those that have a green fluorescent protein (GFP)-like chromophore, and fusions for use in two hybrid selection systems.

For long-term, high-yield recombinant production of the proteins, protein fusions, and protein fragments described herein, stable expression is preferred. Stable expression is readily achieved by integration into the host cell genome of vectors (preferably having selectable markers), followed by selection for integrants.

The polypeptides of the invention may be expressed in any appropriate host cell. The host cell can be prokaryotic (bacteria) or eukaryotic (e.g., yeast, insect, plant and animal cells). A host cell strain may be chosen for its ability to carry out desired post-translational modifications of the expressed protein. Such post-translational modifications of the polypeptide include, but are not limited to, acetylation, carboxylation, glycosylation, phosphorylation, hydroxylation, sulfation, lipidation, and acylation.

Exemplary prokaryotic host cells are *E. coli, Caulobacter crescentus, Streptomyces* species, and *Salmonella typhimurium* cells. Exemplary yeast host cells are *Saccharomyces cerevisiae, Schizosaccharomyces pombe, Pichia pastoris*, and *Pichia methanolica*. Exemplary insect host cells are those from *Spodoptera frugiperda* (e.g., Sf9 and Sf21 cell lines, and EXPRESSF™ cells (Protein Sciences Corp., Meriden, Conn., USA)), *Drosophila* S2 cells, and *Trichoplusia ni* HIGH FIVE® Cells (Invitrogen, Carlsbad, Calif., USA). Exemplary mammalian host cells are COS1 and COS7 cells, NSO cells, Chinese hamster ovary (CHO) cells, NIH 3T3 cells, 293 cells, HEPG2 cells, HeLa cells, L cells, MDCK, HEK293, WI38, murine ES cell lines (e.g., from strains 129/SV, C57/BL6, DBA-1, 129/SVJ), K562, Jurkat cells, BW5147 and any other commercially available human cell lines. Other useful mammalian cell lines are well known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA).

In one embodiment of the instant host vector systems, the host cell is a eukaryotic, bacterial, insect or yeast cell. In a further embodiment, the host cell is a eukaryotic cell (e.g., a mammalian cell).

This invention provides a method for producing the first polypeptide, comprising (a) culturing the first host vector system under conditions permitting polypeptide synthesis by the host vector system, and (b) recovering the polypeptide so produced.

This invention also provides a method for producing the second polypeptide, comprising (a) culturing the second host vector system under conditions permitting polypeptide synthesis by the host vector system, and (b) recovering the polypeptide so produced.

This invention provides a first composition comprising (a) a pharmaceutically acceptable carrier and (b) the first polypeptide.

This invention further provides a second composition comprising (a) a pharmaceutically acceptable carrier and (b) the second polypeptide.

The polypeptides of the invention have immunosuppressive activity and act on T cells only upon activation. Thus, these polypeptides induce antigen specific tolerance. The polypeptides and compositions of the invention are useful for preventing, inhibiting, suppressing or reducing an immune response mediated by antigen-specific activation of T cells. In one embodiment, the immune response is involved in transplant rejection. In another embodiment, the immune response is associated with an autoimmune disease, hypersensitivity or allergy. In yet another embodiment, the immune response is related to an inflammatory disorder.

This invention provides a method for inhibiting the onset of transplant rejection in a subject who has received, or is about to receive, a transplant, comprising administering to the subject a prophylactically effective amount of the first, second or third polypeptide.

This invention further provides a method for treating transplant rejection in a subject who has received a transplant, comprising administering to the subject a therapeutically effective amount of the first, second or third polypeptide.

In one embodiment of the methods for inhibiting the onset of and treating transplant rejection, the transplant is an organ transplant. In another embodiment, the transplant is a tissue transplant or involves the transplantation of cells. Transplanted organs include, for example, heart, kidney, skin, lung, liver, eye, bone, and bone marrow. Transplanted tissue includes, for example, vascular tissue. Transplanted cells include stem cells, e.g., umbilical cord stem cells or adult stem cells, pancreatic islet cells, epithelial cells, endothelial cells, and liver cells. The transplant may also be a prosthetic device, e.g., stent. The transplant may be xenogeneic or allogeneic. Preferably, the subject is human.

In one embodiment, the polypeptide is administered concurrently with a second immunosuppressive agent, such as cyclosporine, OKT3 Antibody, rapamycin, Campath I, anti-CD69 antibody, thymoglobulin, and anti-thymocytic antibody. The polypeptide may also be administered before or after administration of the second immunosuppressive agent. In another embodiment, the polypeptide is administered at the time of transplantation and twice a week for two weeks as is routine for transplants. In another embodiment, the polypeptide is administered to the subject at the onset of or during rejection.

Symptoms associated with rejection of a transplant are well known in the art and include for kidney, increased blood urea nitrogen (BUN) levels, for pancreas, increased glycemia, for heart, lymphocyte infiltrates, and for liver, increased levels of enzymes such as aspartate aminotransferase (SGOT) and alanine aminotransferase (SGPT).

This invention provides a method for treating a subject afflicted with an autoimmune disorder, comprising administering to the subject a therapeutically effective amount of the first, second or third polypeptide.

The autoimmune disorder treated can be any such disorder, and includes, without limitation, rheumatoid arthritis, Crohn's disease, multiple sclerosis, autoimmune diabetes, systemic lupus erythematosus, lupus vulgaris, thyroiditis, Addison's Disease, hemolytic anemia, antiphospbolipid syndrome, dermatitis, allergic encephalomyelitis, glomerulonephritis, Goodpasture's Syndrome, Graves' Disease, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Pulmonary Inflammation, Guillain-Barre Syndrome, and autoimmune inflammatory eye disease. Preferably, in the subject method, the subject is human. In one embodiment, the polypeptide is administered to the subject during a flare-up of an autoimmune attack. The method may further comprise administration of additional immunosuppressive drugs, e.g., cytotoxic agents, cyclosporine, methotrexate, azathioprine, and corticosteroids.

Similarly, allergic reactions and conditions, such as asthma (particularly allergic asthma) or other respiratory problems, may also be treated by a polypeptide of the present invention. These molecules can be used to treat anaphylaxis, hypersensitivity to an antigenic molecule, or blood group incompatibility.

This invention further provides a method for treating a subject afflicted with an inflammatory disorder, comprising administering to the subject a therapeutically effective amount of the first, second or third polypeptide.

The inflammatory disorder treated can be any such disorder, and includes, without limitation, (i) inflammatory diseases such as chronic inflammatory pathologies (including chronic inflammatory pathologies such as, but not limited to, sarcoidosis, chronic inflammatory bowel disease, ulcerative colitis, and Crohn's pathology); (ii) vascular inflammatory pathologies such as, but not limited to, disseminated intravascular coagulation, atherosclerosis, Kawasaki's pathology and vasculitis syndromes (such as, but not limited to, polyarteritis nodosa, Wegener's granulomatosis, Henoch-Schonlein purpura, giant cell arthritis and microscopic vasculitis of the kidneys); (iii) chronic active hepatitis; (iv) Sjogren's syndrome; (v) spondyloarthropathies such as ankylosing spondylitis, psoriatic arthritis and spondylitis, enteropathic arthritis and spondylitis, reactive arthritis and arthritis associated with inflammatory bowel disease; and (vi) uveitis. Preferably, in the subject method, the subject is human. The method can also be combined with administration of additional anti-inflammatory agents. Anti-inflammatory agents include, but are not limited to, any known nonsteroidal anti-inflammatory agent such as, salicylic acid derivatives (aspirin), para-aminophenol derivatives (acetaminophen), indole and indene acetic acids (indomethacin), heteroaryl acetic acids (ketorolac), arylpropionic acids (ibuprofen), anthranilic acids (mefenamic acid), enolic acids (oxicams) and alkanones (nabumetone) and any known steroidal anti-inflammatory agent which include corticosteriods and biologically active synthetic analogs with respect to their relative glucocorticoid (metabolic) and mineralocorticoid (electrolyte-regulating) activities. Additionally, other drugs used in the therapy of inflammation include, but are not limited to, autocoid antagonists such as histamine, bradykinin receptor antagonists, leukotriene and prostaglandin receptor antagonists, and platelet activating factor receptor antagonists.

This invention further provides a method for inducing anergy in a T cell, thereby causing it to differentiate into a regulatory cell, comprising contacting the T cell with the first, second or third polypeptide under conditions permitting priming of the T cell to occur, thereby inducing anergy in the T cell and causing it to differentiate into a regulatory cell. Contacting of the T cell may be performed in vivo, ex vivo or in vitro.

In one embodiment, the T cell is a CD4$^+$ T cell, a CD3$^+$ cell or a CD8$^+$ T cell, and the conditions permitting priming to occur comprise contacting the T cell with an allogeneic stimulator (e.g., an allogeneic antigen presenting cell (APC)) or an autologous APC that has been pulsed with an antigen. Exemplary antigen presenting cells include dendritic cells, monocytes, macrophages, endothelial cells and epithelial cells. In the preferred embodiment, the allogeneic stimulator is an irradiated KG1 cell.

This invention further provides a method for treating a subject afflicted with an autoimmune disorder, comprising contacting, ex vivo, the first, second or third polypeptide with T cells obtained from the subject, wherein the contacting is performed under conditions permitting priming of the cells to occur, and intravenously administering the resulting cells to the subject, so as to treat the subject.

This invention also provides a method for treating transplant rejection in a subject, comprising the steps of contacting, ex vivo, T cells obtained from the subject with a polypeptide of the invention (e.g. the first, second or third polypeptide) under conditions permitting priming of the cells, and administering the resulting cells to the subject.

Methods of treating inflammatory disease or graft versus host disease in a subject by treating T cells obtained from the subject with a polypeptide of the invention ex vivo and then administering the treated T cells to the subject are also contemplated.

In one embodiment, the T cell is a $CD4^+$ T cell, a $CD3^+$ T cell or a $CD8^+$ T cell and the conditions permitting priming to occur comprise contacting the T cell with an allogeneic stimulator (e.g., an allogeneic antigen presenting cell (APC)) or an autologous APC that has been pulsed with an antigen. Exemplary antigen presenting cells include dendritic cells, monocytes, macrophages, endothelial and epithelial cells. In the preferred embodiment, the allogeneic stimulator is an irradiated KG1 cell.

Determining an effective amount of the instant polypeptides for use in the instant invention can be done based on animal data using routine computational methods. In one embodiment, the effective amount, administered intravenously, is between about 0.5 mg/kg and about 50 mg/kg of polypeptide. In another embodiment, the effective amount, administered intravenously, is between about 1 mg/kg and about 20 mg/kg of polypeptide. In the preferred embodiment, the effective amount, administered intravenously, is about 3, 5 or 10 mg/kg of polypeptide. In one embodiment of the instant methods, the polypeptide is administered in a single dose. In another embodiment, the polypeptide is administered in multiple doses.

Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the polypeptides or compositions of this invention, including isolated and purified forms, may be accomplished using any of the conventionally accepted modes of administration of agents which are used to prevent or treat transplantation rejection or to treat autoimmune or inflammatory disorders.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The compositions of this invention may, for example, be placed into sterile, isotonic formulations with or without cofactors which stimulate uptake or stability. The formulation is preferably liquid, or may be lyophilized powder. For example, the compositions or polypeptides of the invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions of the present invention can also be formulated so as to provide slow or controlled-release of the active ingredient therein using, e.g., hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

Also provided are methods of delivering membrane-bound polypeptides of the invention using lipid bilayers or by administration of cells manipulated to express the polypeptides of the invention (e.g., cells transfected with a nucleic acid encoding a polypeptide of the invention) (M. Davis et al., JCB 166:579-590 (2004)).

Nucleic acids encoding a polypeptide of the invention may be administered using gene therapy methods. Retrovirus vectors and adeno-associated virus (AAV) vectors are preferred vectors according to the invention for transferring nucleic acids encoding the polypeptides of the invention into cells in vivo, particularly into human cells. These vectors provide efficient delivery of genes into cells, and the transferred nucleic acids are stably integrated into the chromosomal DNA of the host. The development of specialized cell lines ("packaging cells") that produce replication-defective retroviruses are especially preferred for gene therapy applications (see, e.g., Miller, A. D. Blood 76:271 (1990)). Recombinant retrovirus may be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses may be found, e.g., in Current Protocols in Molecular Biology, Ausubel, F. M. et al. (eds.) Greene Publishing Associates, (1989), Sections 9.10-9.14 and other standard laboratory manuals. Representative examples of retroviruses include pLJ, pZIP, pWE and pEM which are well known to those skilled in the art. Representative examples of packaging virus lines for preparing both ecotropic and amphotropic retroviral systems include psi.Crip, psi.Cre, psi 2 and psi.Am. Retroviruses have been widely used to introduce a variety of genes into many different cell types in vitro and/or in vivo. Moreover, it is useful to limit the infection spectrum of retroviruses and retroviral-based vectors by modifying the viral packaging proteins on the surface of the viral particle (see, for example PCT publications WO93/25234 and WO94/06920; Roux et al. PNAS 86:9079-9083 (1989); Julan et al. J. Gen Virol 73:3251-3255 (1992); and Goud et al. Virology 163: 251-254 (1983)); Neda et al. J. Biol Chem 266:14143-14146 (1991)).

This invention further provides an article of manufacture comprising (a) a packaging material having therein the first polypeptide, and (b) a label indicating a use for the polypeptide for (i) treating or inhibiting the onset of transplant rejection in a subject, (ii) treating an autoimmune disorder in a subject, or (iii) treating an inflammatory disorder in a subject.

Finally, this invention provides an article of manufacture comprising (a) a packaging material having therein the second polypeptide, and (b) a label indicating a use for the polypeptide for (i) treating or inhibiting the onset of transplant rejection in a subject, (ii) treating an autoimmune disorder in a subject, or (iii) treating an inflammatory disorder in a subject.

This invention will be better understood from the Experimental Details which follow. However, one skilled in the art will readily appreciate that the specific methods and results discussed are merely illustrative of the invention as described more fully in the claims which follow thereafter.

Experimental Details

The most extensively studied "protein therapeutic drugs" are (1) monoclonal antibodies, (2) cytokine-fusion proteins and (3) chimeric cell adhesion molecules that prevent T cell activation and/or proliferation.

Soluble ILT3 ("sILT3") (encompassing the first and second instant polypeptides) belongs to the family of chimeric proteins that modulate the immune system. sILT3 is an attractive candidate for therapeutic use based on its potent in vitro immune modulating activities and orthologue (homolog) of ILT3 studies shown in animal models of acute and chronic inflammation, autoimmunity. Soluble ILT3 induces immune tolerance by inhibition of T cell activation that contributes to graft rejection.

Examples of soluble chimeric proteins being investigated in clinical trials are CTLA-4, CD86, PD-1 and PD-L1 fusion proteins. Some have been proven effective against specific autoimmune disease. However, these molecules behave both stimulatory and inhibitory manner depending on their counter-receptors. Furthermore, their expression is ubiquitous such that CTLA-4 and its counter-receptor are expressed on the same T cells. Moreover, the broad expression pattern of their counter-receptors on B cell, DCs, ECs, macrophages, fibroblasts, muscle cells and trophoblast cells render them less-specific for the inhibition of T cell proliferation.

In this respect, ILT3 is unique. Its expression is limited to dendritic (professional) and endothelial (semi-professional) antigen presenting cells, two cell types playing an important role in modulating the immune responses. They can be either immunogenic or tolerogenic. However, the expression of ILT3 on these two cell types renders them tolerogenic leading to induction of anergy. ILT3 can be induced with inhibitory cytokines (IL10, IFNα) and VitD3 and render DC and EC tolerogenic. However, one can not ignore the possible other, as yet undiscovered effects of cytokine treatments on cells. Thus, having sILT3 directly interact with T cells, rendering them anergic, will be more effective in down-regulating the immune system.

This invention offers several advantages. First, the second polypeptide of this invention has an extended circulating half-life and provides long-term protection, acting as a long-lasting "chimeric" protein drug. The prolonged half-life permits lower dosing, thereby reducing toxicity. Second, soluble polypeptides (i.e. the extracellular domain of ILT3) and longevity-increasing polypeptides (i.e., Fc portion of Ig) useful in this invention can readily be isolated using routine methods.

EXAMPLE 1

Construction of Cells Expressing ILT3 or ILT3delta

KG1 cells over-expressing human ILT3 (KG1.ILT3 cells) were generated as previously described (CC Chang et al., Nat. Immunol. 3:237-243, 2002). Deletion of the cytoplasmic region of ILT3 was accomplished by PCR amplification using the following primers: sense-5'-CCATGATATCAG-GAGACGCCATGATCCCCA-3' (SEQ ID NO: 1) and anti-sense-5'-ATGTAGCGGCCGCGTTTTCTCCCTG-GACGTCA-3' (SEQ ID NO: 2) and a plasmid containing a full-length cDNA of ILT3 (pcDNA4-ILT3) was used as template. PCR conditions were as follows: 5 min 94° C.; 30 cycles (30 sec 94° C., 1 min 68° C., 1 min 72° C.); 7 min 72° C. The PCR product was purified using a PCR purification kit (Qiagen) and subcloned into the EcoRV and NotI sites of the expression vector pcDNA4/TO/myc-His in frame with a c-myc-His epitope (Invitrogen). The resulting ILT3 deletion mutant, ILT3delta (which contains residues 1 (Met) to 328 (Asn) of human ILT3), encodes a protein that contains the putative leader peptide, the extracellular and transmembrane domains and a stretch of 48 amino acids of the cytoplasmic domain of ILT3 followed by a C-terminal myc-His tag. The ILT3delta insert was subcloned into the BglII site of retroviral vector MIG(MSCV-IRES-GFP) and the resulting construct was confirmed by sequencing. The ILT3delta was over-expressed in KG1 cells by retroviral transduction (Chang et al., supra). Transfectants were sorted for GFP expression by flow cytometry.

Generation of Soluble ILT3-Fc Chimeric Protein cDNA fragment coding for the extracellular domain of human ILT3 was fused to the Fc portion of the human IgG1 heavy chain. To abolish binding to the Fc receptor, a mutation was introduced in the N-linked glycosylation site, N77 (Asn>Gln) of the Fc domain. Expression vector pcDNA3 (Invitrogen) containing the ILT3-Fc fusion gene (FIG. 1) was transfected into CHO-S cells. Homogenous cell populations were obtained by limiting dilution and clones with high expression of ILT3 (as determined by RT-PCR and Western Blot analysis) were selected. ILT3-Fc fusion proteins were purified from the supernatant of the selected clones using a recombinant protein A FF column and analyzed by Western blotting using an anti-human Fc-specific antibody.

EXAMPLE 2

Figure 4A:
FIGS. 4A-4D
(A) Schematic diagram of MIG retroviral expression vectors of ILT3 and ILT3 delta. (B) Fluorescence histograms of ILT3 expression on the surface of KG1.ILT3 and KG1.ILT3delta. (C) Confirmation of the molecular weight of ILT3delta by Western Blot and determination of inability of ILT3delta molecule to recruit SHP-1 by immunoprecipitation and Western blot. (D) Inhibition of protein tyrosine phosphorylation in KG1.ILT3 but not in KG1.ILT3delta cells by crosslinking anti-HLA-DR and anti-ILT3 mAbs.
Figure 4A:
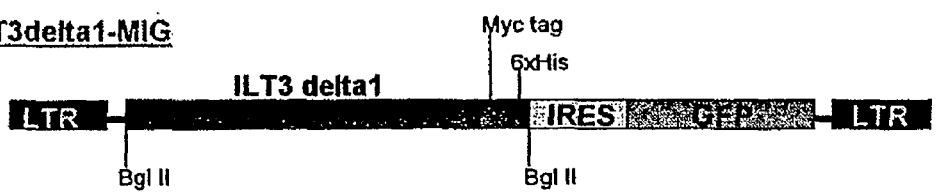
Figure 4A:
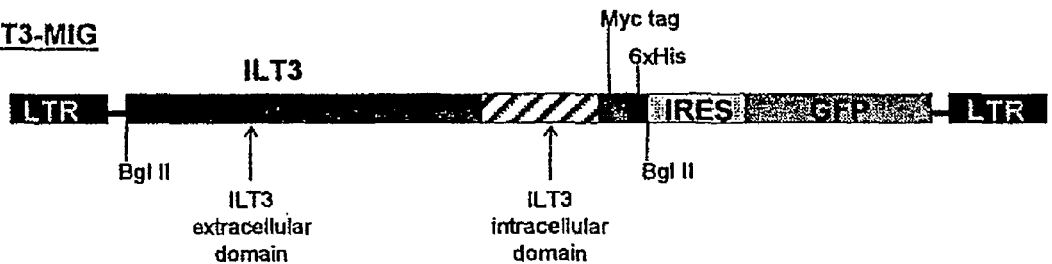

Membrane ILT3 Induces $CD4^+$ $T_H$ Cell Anergy and Inhibits the Generation of $CD8^+$ Cytotoxic Cells The cytoplasmic region of ILT3 contains ITIM motifs that recruit inhibitory phosphatases, which can negatively regulate cell activation. The extracellular portion contains two Ig domains, one or both of which are likely to contribute to the ILT3 ligand binding sites involved in the interaction of APC with T lymphocytes. By overexpressing the cytoplasmic tail deletion mutant ILT3delta in KG1 cells, we generated the KG1.ILT3delta cell line, which we then used to explore the activity of membrane ILT3 (mILT3) (FIG. 4A).

Figure 4B:
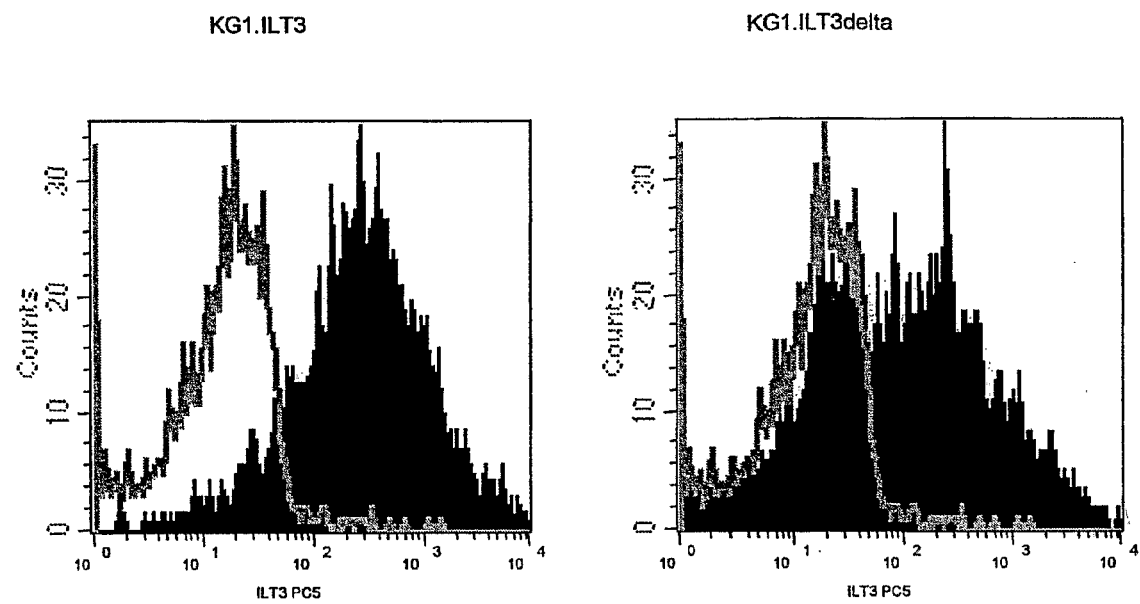
Figure 4C:
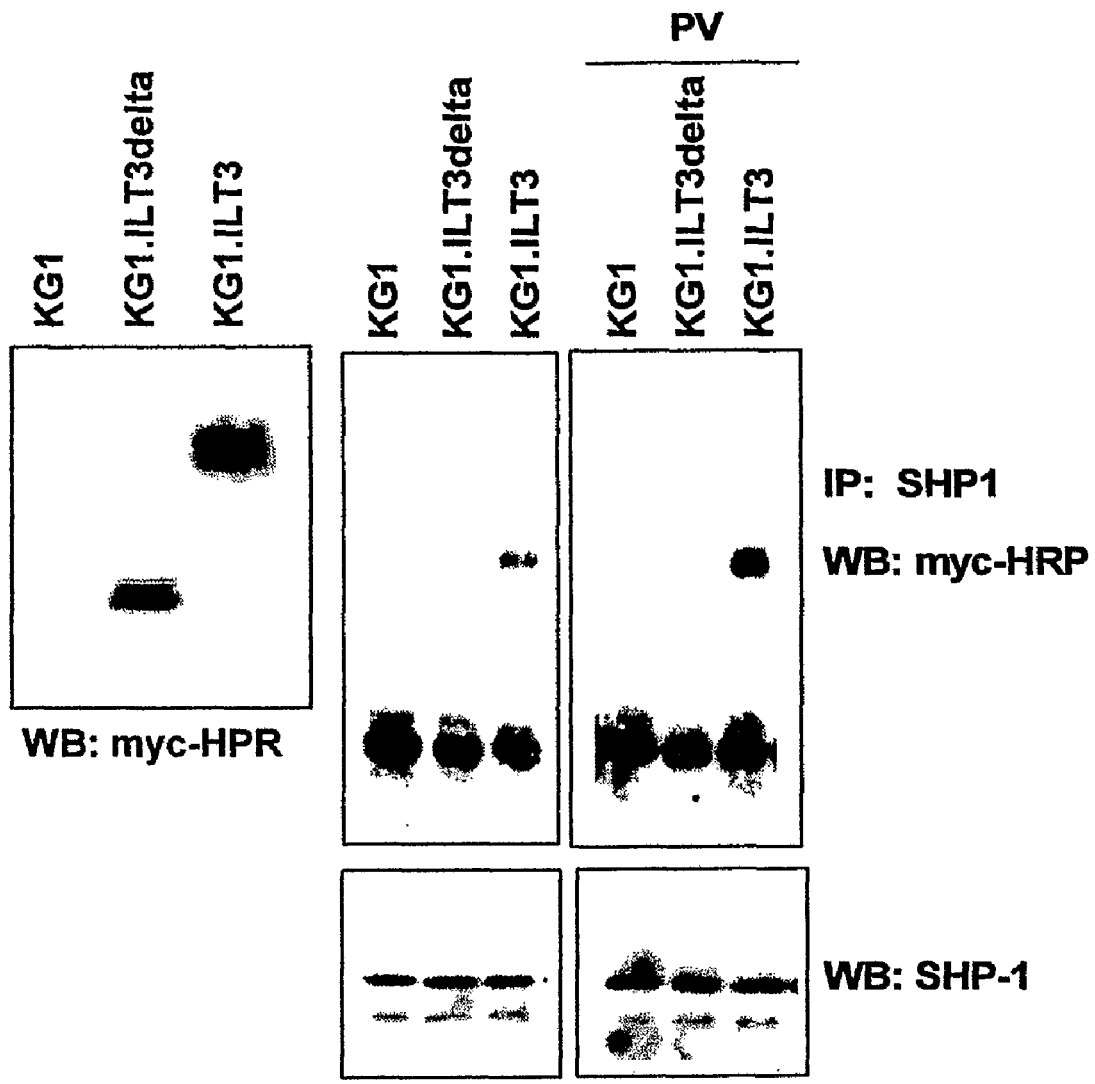

KG1.ILT3 and KG1.ILT3delta expressed similar amounts of ILT3 protein on the cell surface as shown by flow cytometry analysis using mAb to ILT3 (FIG. 4B). Western blot analysis using anti-myc antibody, which binds to the C-terminal myc tag of the recombinant proteins, demonstrated that the molecular weight of the ILT3delta protein was 38 kDa while that of full length ILT3 was 50 kDa (FIG. 4C).

ILT3 associates with SHP-1 phosphatase and this association is increased by receptor crosslinking with specific antibodies or with pervanadate treatment. SHP-1 recruitment upon phosphorylation of the cytoplasmic ITIMs has been shown to mediate the negative signaling of ILT2, a closely related member of the same family of Ig-like inhibitory receptors as ILT3. Immunoprecipitation experiments using the anti-SHP-1 antibodies and western blot analysis using an anti-myc antibody showed constitutive interaction of the full-length ILT3 molecule and SHP-1. As expected, no interaction of SHP-1 with ILT3delta was observed (FIG. 4C).

Figure 4D:
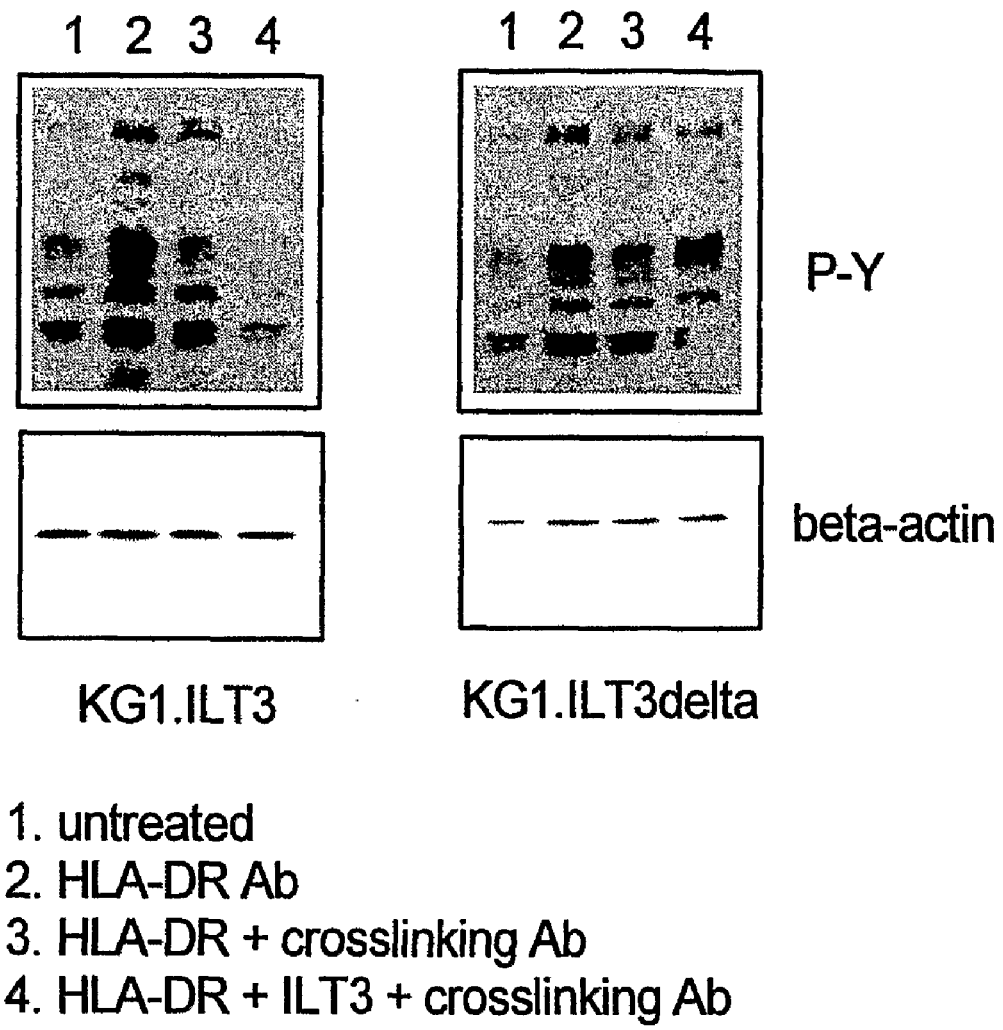

Antibodies against HLA-DR can trigger both $Ca^{2+}$ mobilization and specific protein phosphorylation. Co-crosslinking of the anti-HLA-DR antibody with anti-ILT3 antibody results in substantial inhibition or more rapid extinction of the activation signal (Cella et al., J. Exp. Med., 185:1743-1751, 1997). To establish whether lack of SHP-1 recruitment by ILT3delta was accompanied by a lack of inhibition of protein tyrosine phosphorylation, KG1.ILT3 and KG1.ILT3delta cells were ligated with anti-HLA-DR mAb or with anti-HLA-DR mAb and anti-ILT3 mAb in the presence of a crosslinking antibody. Total cell extracts were analyzed by western blot with anti-phosphotyrosine mAb and reprobed with anti-β-actin mAb for control of equal loading. The results showed that crosslinking HLA-DR and ILT3 on KG1.ILT3 cells inhibits tyrosine phosphorylation, however, it has little or no effect on tyrosine phosphorylation in KG1.ILT3delta mutants (FIG. 4D).

Figure 5A:
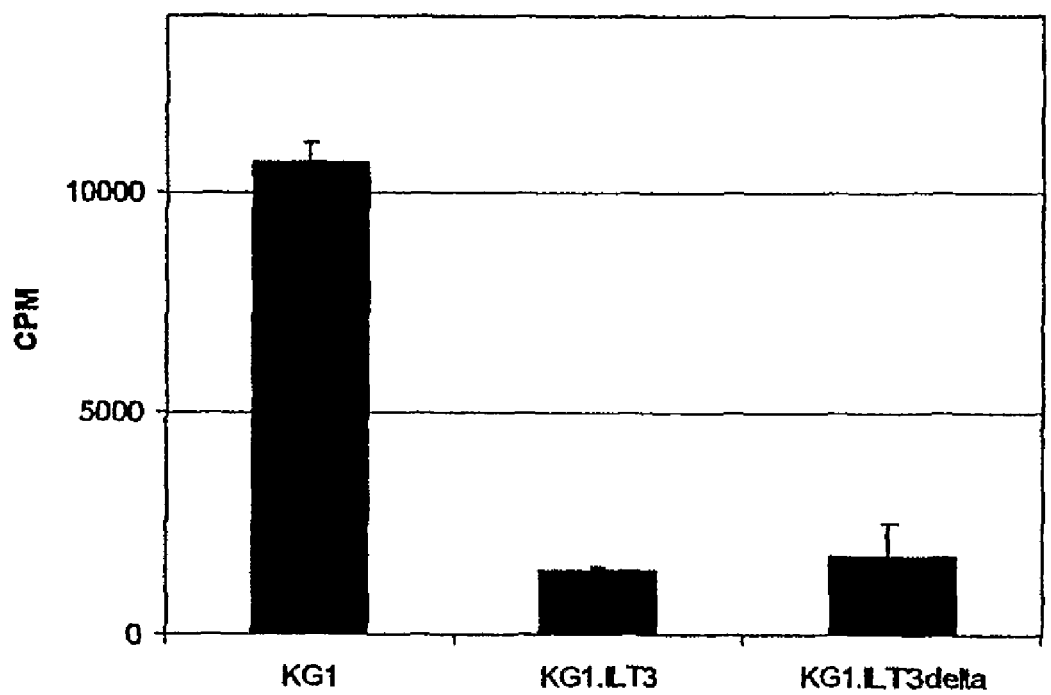
FIG. 5A-5C
(A) ILT3 and ILT3delta molecules inhibit proliferation of CD3+CD25− T cells in 5 day primary MLCs. (B) ILT3 and ILT3delta molecules suppress proliferation of CD4+ T cells primed with KG1 cells in 3 day secondary MLC, which can be reversed by addition of IL-2 or anti-ILT3 mAb. (C) CD8+ T cells primed with KG1, but not with KG1.ILT3 are cytotoxic to KG1 cells at ET ratio of 1 to 1.

Comparison of the capacity of KG1, KG1.ILT3 and KG1.ILT3delta to elicit T cell proliferation in primary and secondary MLC showed that KG1.ILT3 and KG1.ILT3delta elicited much less proliferation of unprimed (FIG. 5A) or KG1-primed T cells (FIG. 5B) than KG1 cells.

For the proliferation assays, responding T cells ($5\times10^4$/well) were tested for reactivity to irradiated KG1, KG1.ILT3, KG1.ILT3delta, or allogeneic CD2-depleted APC ($2.5\times10^4$/well). After 5 days (for naive T cells) or 2 days (for primed T cells) of incubation, the cultures were pulsed with [$^3$H]-thymidine and harvested 18 hours later. [$^3$H]-thymidine incorporation was determined by scintillation spectrometry in an LKB 1250 Betaplate counter. Mean counts per minute (c.p.m.) of triplicate cultures and the standard deviation (sd) to the mean were calculated.

Figure 5B:
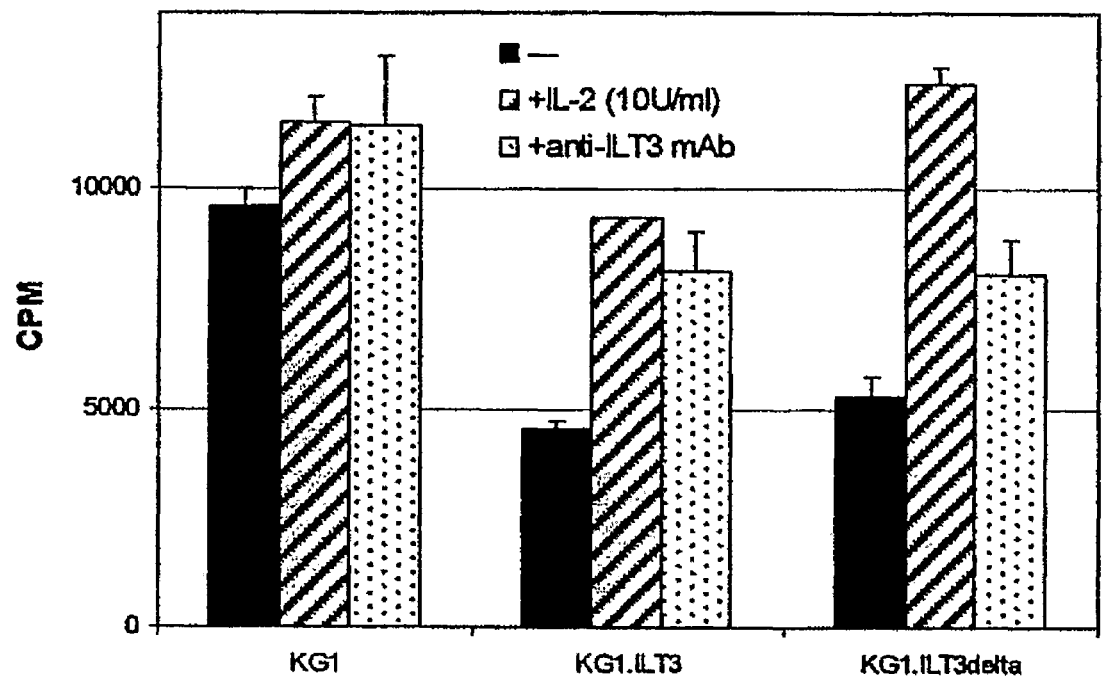

Addition of anti-ILT3 monoclonal antibody (5 μg/ml) or IL-2 (10 U/ml) to the blastogenesis assays restored T cell proliferation in response to KG1.ILT3 and KG1.ILT3delta (FIG. 5B). These experiments indicate that mILT3 protein is sufficient for inducing an inhibitory signal in activated T cells and that deletion of the cytoplasmic region of ILT3 does not abrogate its T cell anergizing activity.

Figure 5C:
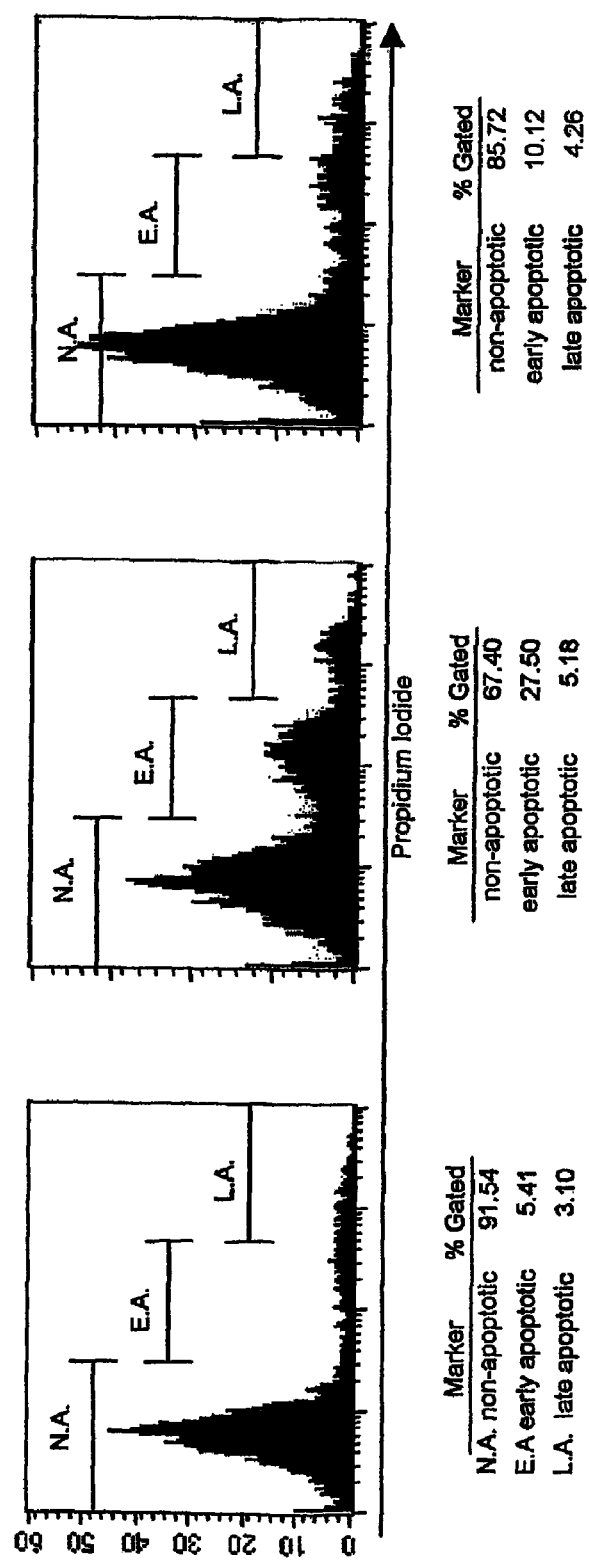

To study the effect of ILT3 on the generation of cytotoxic T cells, $CD3^+CD25^-$ T cells were primed with KG1, KG1.ILT3 or KG1.ILT3delta. After 7 days, $CD8^+$ T cells were isolated from each of the cell cultures and tested for their ability to kill KG1 cells. T cells primed with KG1.ILT3 or KG1.ILT3delta showed significantly less cytotoxic activity (6%) than T cells primed with KG1 (24%) as determined by Annexin V/Propidium Iodine staining (FIG. 5C) and produced less IFN-gamma. Thus, T cell interaction with mILT3 inhibits the differentiation of cytotoxic effector cells.

sILT3 Induces $CD4^+$ $T_H$ Cell Anergy and Inhibits the Generation of $CD8^+$ Cytotoxic Cells sILT3 expression was assayed by Western blotting. Briefly, cell extracts at equal concentration were immunoprecipitated from cleared extract using mouse anti-ILT3 mAb (ZM 3.8) and subjected to SDS-PAGE. Proteins were then electrotransferred onto polyvinylidene difluoride (PVDF) membrane, and were incubated with anti-human Fc polyclonal antibody. Immunoblots were developed by ECL and acquired by the phosphor/fluorescence imager. Apparent molecular weight of soluble ILT3 is about 90 and 50 kDA in non-reducing and reducing conditions, respectively.

Figure 3A:
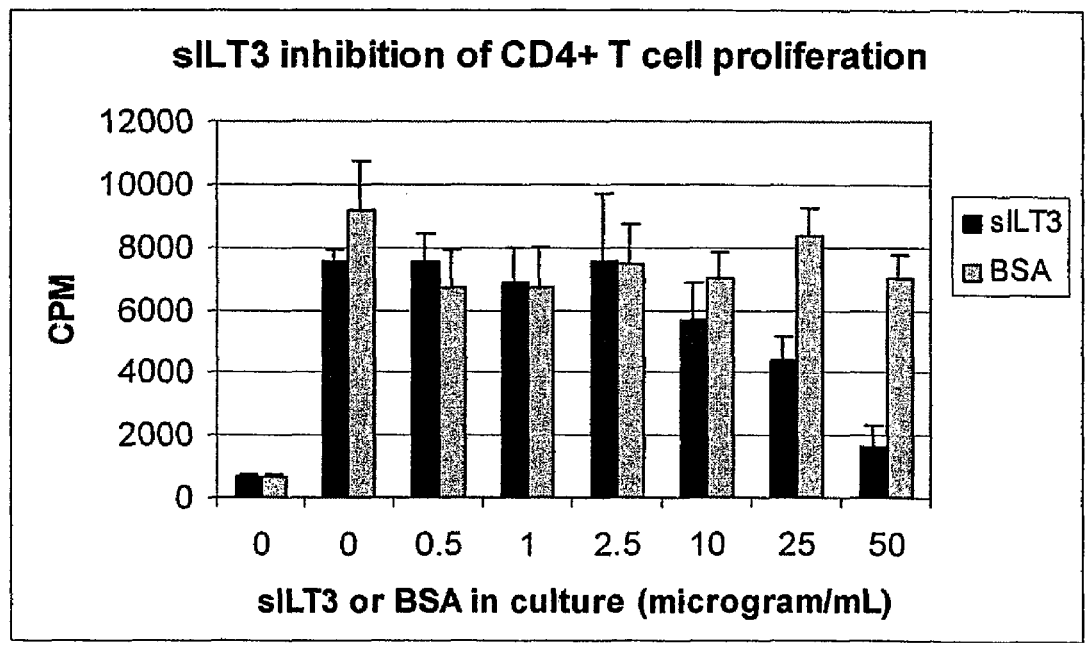
FIGS. 3A-3B
(A) Soluble ILT3 inhibits T lymphocyte proliferation in vitro. (B) Inhibition is abrogated by anti-ILT3 antibody.
Figure 3B:
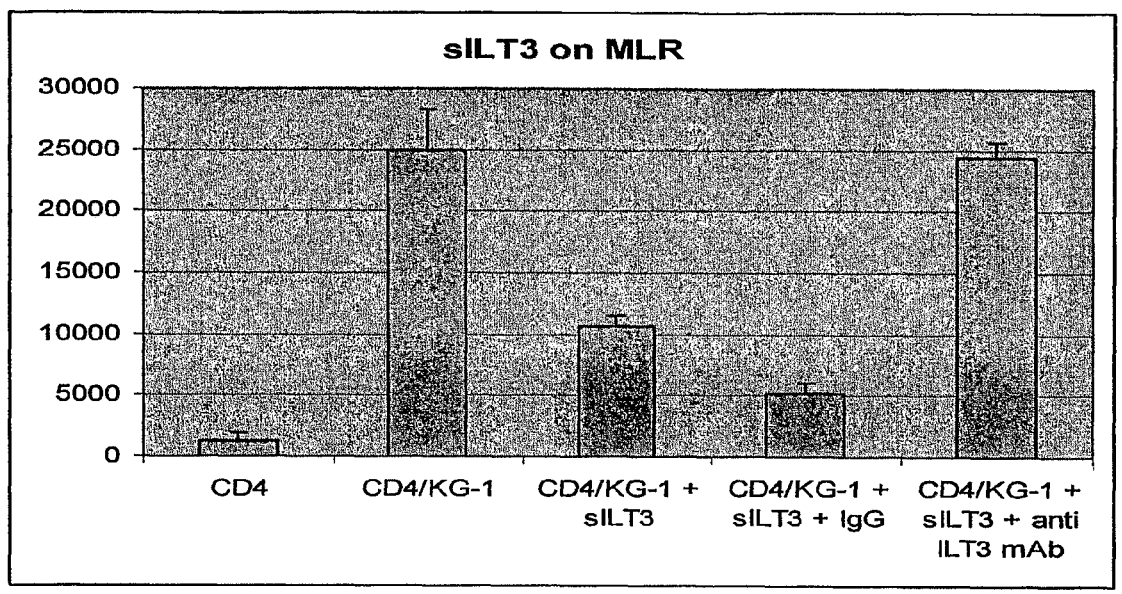
Figure 6:
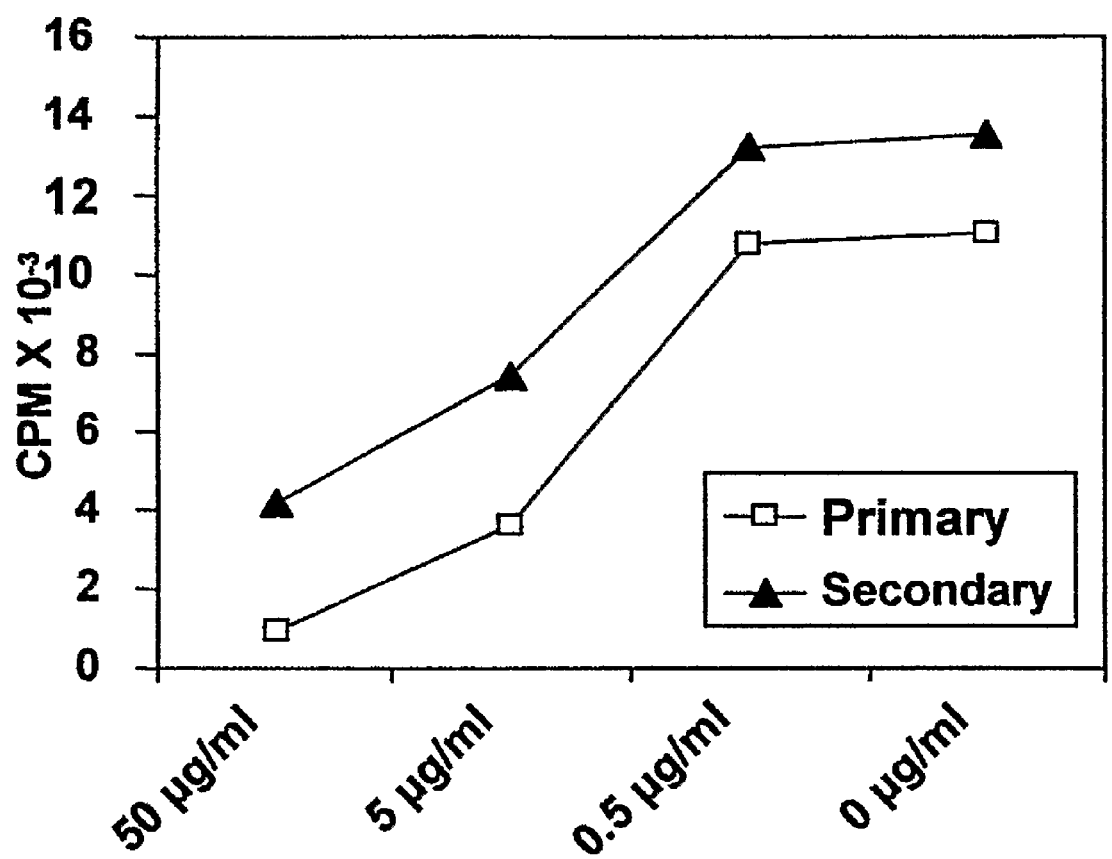
FIG. 6
sILT3 suppress proliferation of CD3+ CD25− T cells in primary and secondary MLCs.

Responding $CD3^+CD25^-$ or $CD4^+CD25^-$ cells ($1\times10^5$ cells/well) were stimulated with irradiated KG-1 cells (30 min) ($0.5\times10^5$ cells/well) in the presence or absence of sILT3-Fc fusion protein in 96-well, round bottom microtiter plates. At 5 days later, cell proliferation was determined by pulsing with [$^3$H]thymidine (0.5 μCi/well) overnight and radioactivity was counted on a beta reader. Addition of 50 μg/ml sILT3 inhibited cell proliferation by >90% (FIGS. 3 and 6). Similarly, when 50 μg/ml sILT3 was added to secondary MLC at the time of restimulation there was >70% inhibition of the secondary response (FIG. 6).

Figure 7:
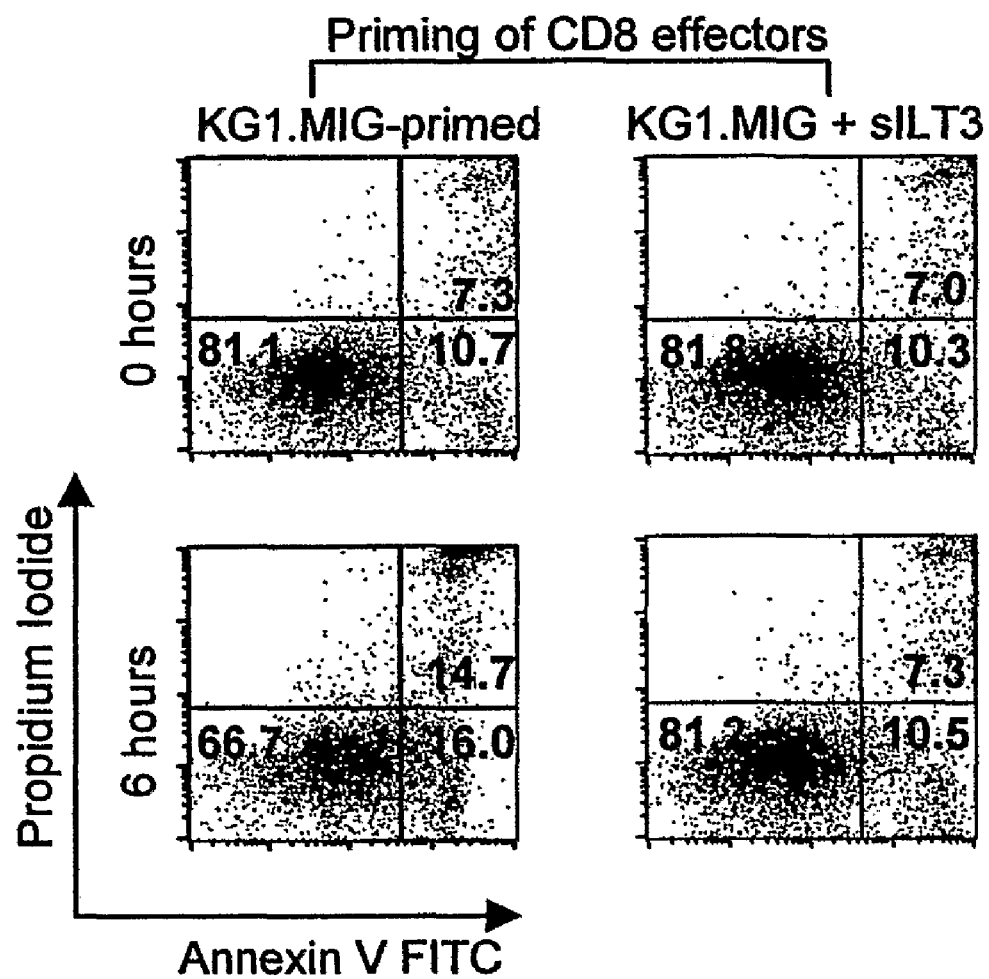
FIG. 7
sILT3 inhibit generation CD8+ cytotoxic T cells.
Figure 8:
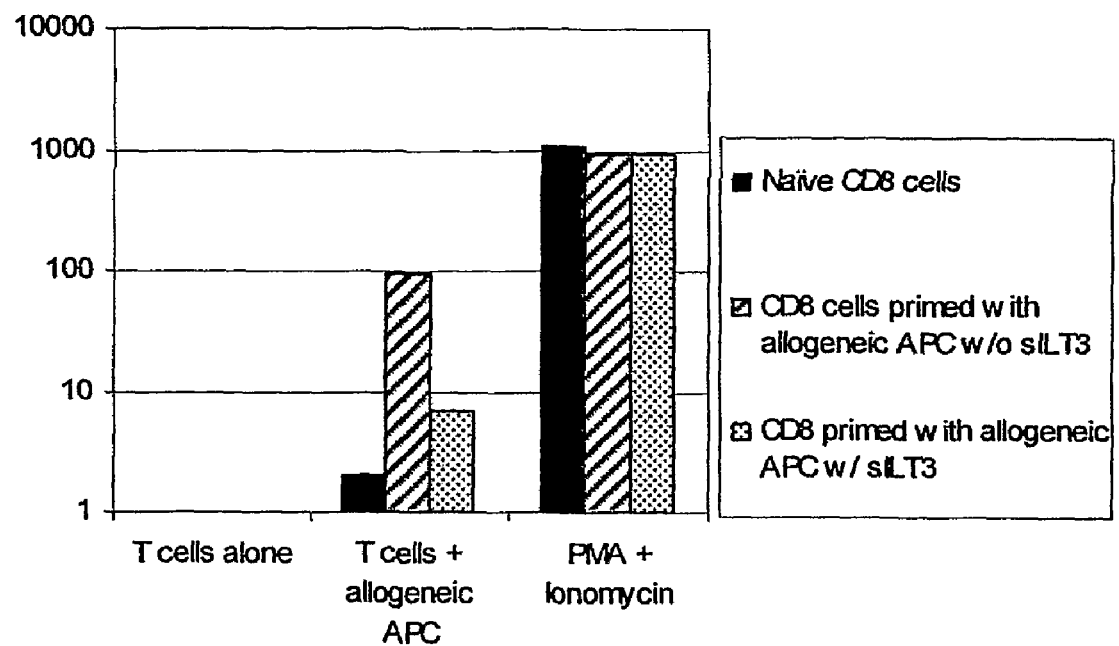
FIG. 8
Frequency of IFN-γ producing CD8+ T cells from T cells primed with allogeneic APC with sILT3 is higher than CD8+ T cells primed with the same APC without sILT3.

Analysis of the capacity of sILT3 to inhibit generation of cytotoxic T cells showed that $CD8^+$ T cells primed in 7-day cultures with KG1 cells, in the presence of sILT3 (50 μg/ml) were devoid of killing capacity (FIG. 7). Furthermore, $CD8^+$ T cells from these cultures did not produce IFN-gamma as demonstrated in ELISPOT assays (FIG. 8). Taken together these data indicate that sILT3, similar to mILT3, induces $T_H$ anergy and blocks the generation of cytotoxic T cells.

EXAMPLE 3 mILT3 and sILT3 Induce the Generation of Regulatory/Suppressor T Cells

The finding that sILT3 inhibits T cell proliferation in response to allogeneic stimulating cells suggested the possibility that this protein induces anergy in primed T cells triggering their differentiation into regulatory cells.

To explore this hypothesis, umprimed $CD4^+$ or $CD8^+$ T cells were incubated with allogeneic stimulators (irradiated KG1 cells) in the presence or absence of sILT3 (50 μg/ml). After 7 days, T cells were harvested from the cultures and tested for: (a) expression of FOXP3 (a T suppressor/regulatory cell marker) and (b) capacity to inhibit MLC reactions.

Figure 9A:
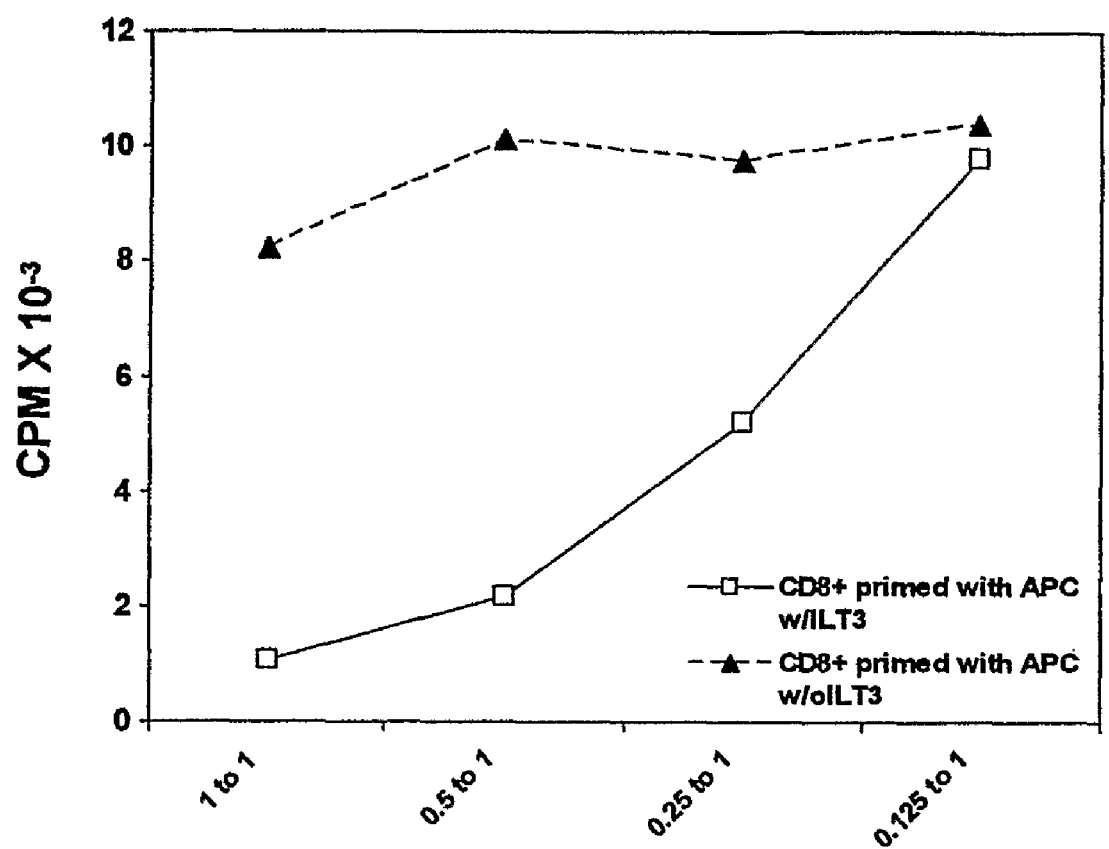
FIG. 9A-9D
(A) CD8+ T cells primed with allogeneic APC in the presence of sILT3, but not in the absence of sILT3 suppress proliferation response of naïve $CD3^+CD25^-$ T cells from the same responder to the original stimulator. (B) $CD8^+T$ cells primed with KG1.ILT3, but not KG1 suppress proliferation response of naïve $CD3^+CD25^-$ T cells from the same responder KG1 cells. (C) $CD8^+$ T cells primed with allogeneic APC with sILT3, but not without sILT3, or primed with KG1.ILT3 cells, but not with KG1 cells express high FOX3 protein in Western blot analysis. (D) $CD8^+$ T cells primed with allogeneic APC with sILT3, but not without sILT3 up-regulate ILT3 expression and down-regulate CD86 expression on immature DC derived from the same stimulator for priming.

$CD4^+$ and $CD8^+$ T cells primed in the presence of sILT3 for 7 days expressed FOXP3 and suppressed KG1-triggered proliferation of naïve $CD4^+$ T cells in MLC. Control T cells primed for 7 days in cultures with sILT3 or with sILT3 but without allogeneic stimulating cells did not acquire regulatory function. $CD8^+$ T cells primed in the presence of sILT3 induced dose-dependent inhibition of T cell proliferation from 50% at a 0.25:1 ratio of primed $CD8^+$ $T_S$ to responding $CD4^+$ $T_H$ cell ratio to 90% at a 1:1 ratio (FIG. 9A). $CD8^+$ T cells primed in cultures without sILT3 induced 20% inhibition at the highest concentration and virtually no inhibition at lower doses.

Figure 9B:
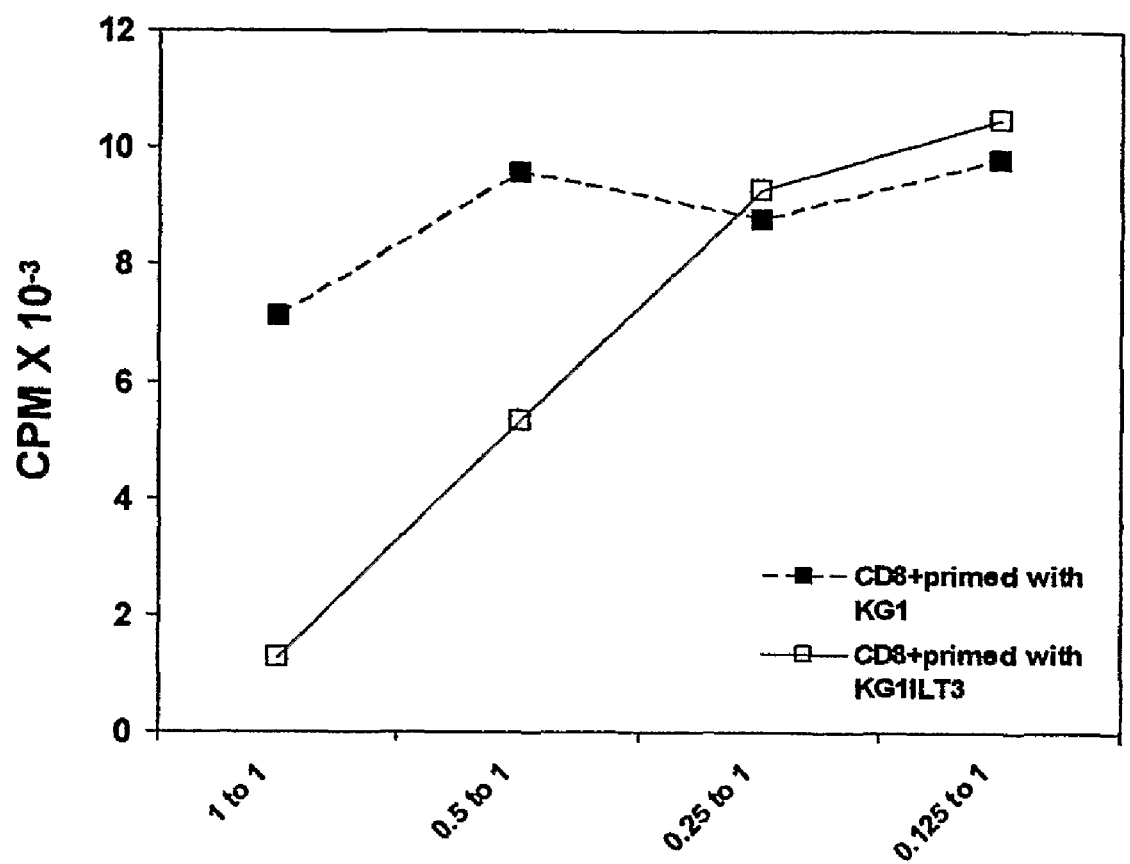

The capacity of mILT3 to induce the generation of $CD8^+$ T suppressor cells was also tested. $CD3^+CD25^-$ T cells were primed for 7 days either with KG1 or KG1-ILT3delta cells and then $CD8^+$ T cells were isolated and tested for their capacity to inhibit the response of unprimed, autologous $CD4^+$ T cells to KG1. $CD8^+$ T cells primed to KG1-ILT3 induced dose-dependent inhibition of T cell response to KG1 while $CD8^+$ T cells primed to KG1 showed inhibitory activity (35%) only at a 1:1 ratio (FIG. 9B).

Figure 9C:
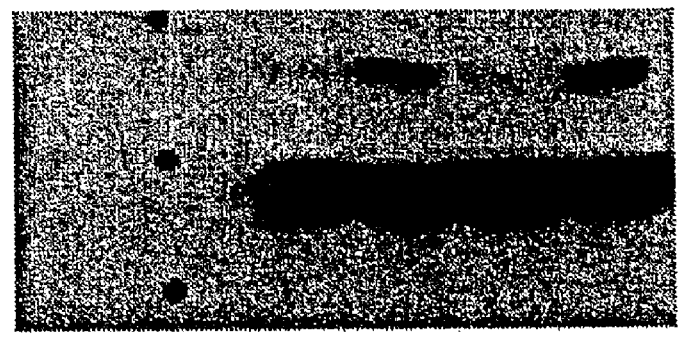
Figure 9C:
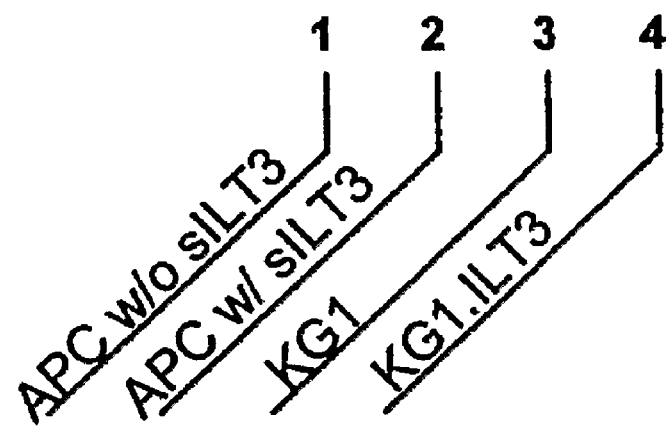

Therefore sILT3 as well as mILT3 induces the differentiation of $CD8^+$ T suppressor cells in primary MLC. Since FOXP3 is a characteristic marker for $CD4^+$ and $CD8^+$ regulatory T cells, its expression in $CD8^+$ T cells primed for 7 days to allogeneic APC in the presence or absence of sILT3 (50 μg/ml) was determined. $CD8^+$ T cells from cultures stimulated either with KG1 or with KG1.ILT3delta were also tested for FOXP3 expression. Western Blot analysis using mAb to FOXP3 (FIG. 9C) showed that both sILT3 and mILT3 induced CD8+ T cells with suppressor activity and high expression of FOXP3. Taken together these data indicate that both sILT3 and mILT3 induce the differentiation of CD8+ $T_S$ with potent inhibitory activity.

EXAMPLE 4 sILT3 induces the Generation of CD8+ T Suppressor Cells by Interaction with CD4+ T Cells CD8+ T suppressor cells generated by multiple in vitro stimulation with allogeneic APC were previously shown to act directly on APC, inducing the down regulation of costimulatory molecules and the upregulation of ILT3 and ILT4. To determine whether T suppressor cells generated by allostimulation in the presence of sILT3 have a similar effect on APC, we tested CD8+ T cells primed under such conditions for their ability to modulate CD86 and ILT3 expression on DC from the donor used for priming and on control DC from an individual sharing no HLA class I antigens with the original stimulator.

Figure 9D:
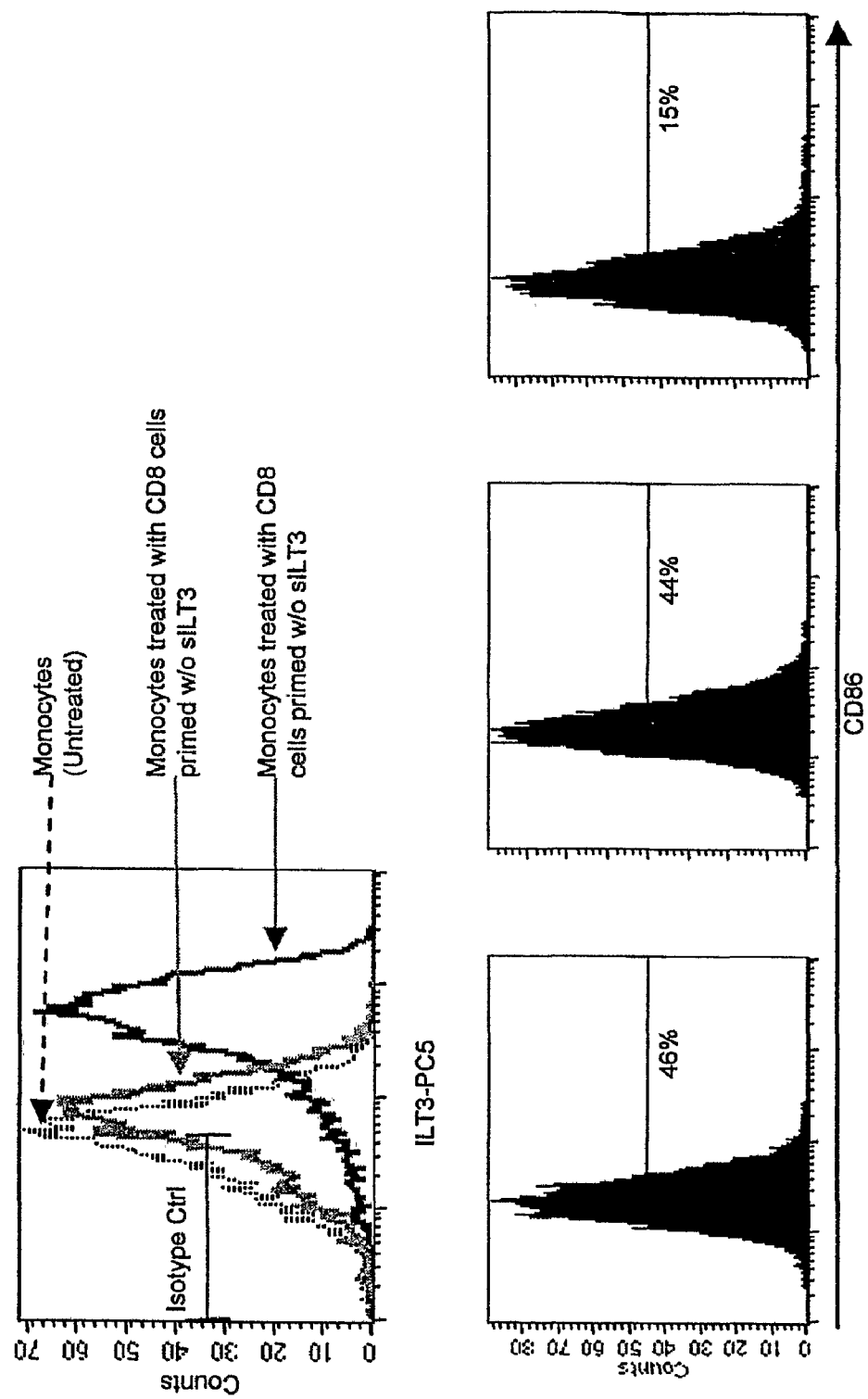

CD8+ T cells isolated from the culture containing sILT3 were able to dramatically upregulate the expression of ILT3 on DC from the specific stimulator but not on control APC. This alloantigen-specific upregulation of the inhibitory receptor ILT3 occurred in conjunction with the downregulation of CD86 (FIG. 9D).

Figure 10A:
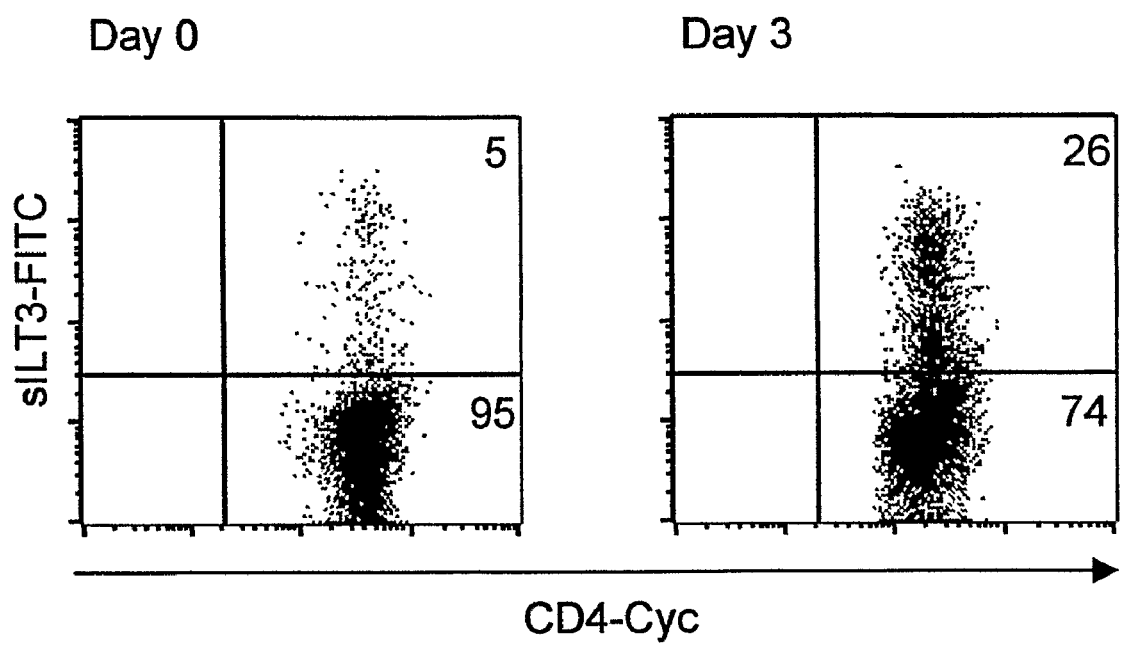
FIG. 10
FITC-labeled sILT3 proteins stains allogeneic APC activated $CD4^+$ T cells at day 3 of primary MLC culture, but not activated $CD8^+$ T cells and naïve $CD4^+$ and $CD8^+$ T cells.
Figure 10B:
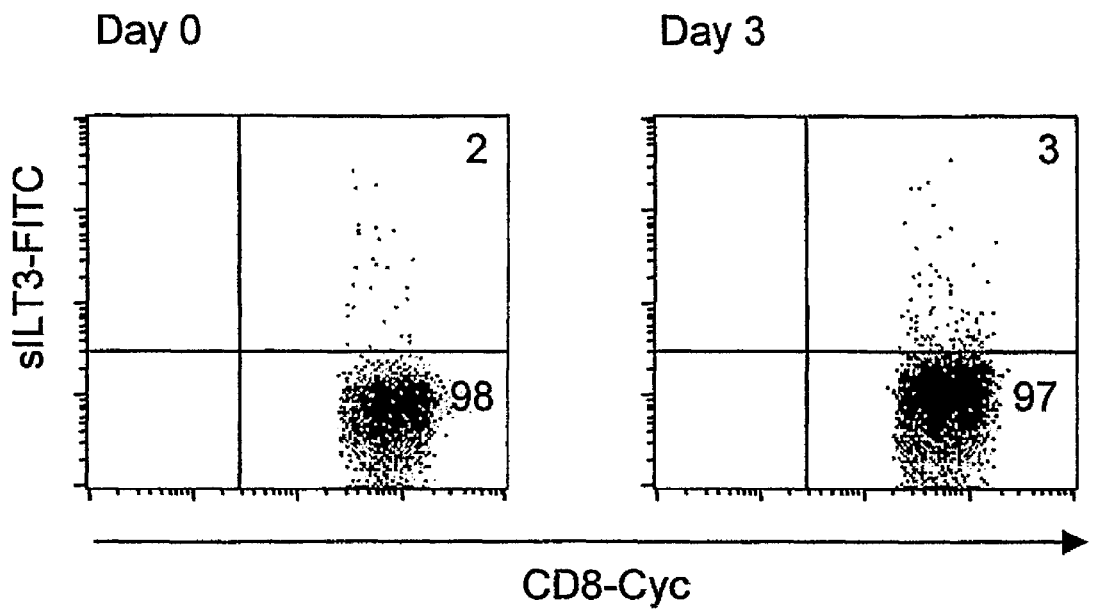

To determine if the generation of CD8+ T suppressor cells is due to direct interaction of ILT3 with CD8+ T cells or if it results indirectly from interaction between ILT3 and CD4+ T cells, FITC-labeled sILT3 protein was used to stain T cells in primary MLC. CD4+ T cells, but not CD8+ T cells were stained by sILT3-FITC indicating that direct interaction of ILT3 and CD8+ cells is not involved in the generation of CD8+ T suppressor cells (FIG. 10).

The discovery that sILT3 has potent immunosuppressive activity and that it acts on T cells only upon activation has important clinical implication indicates that sILT3 is useful for inducing antigen specific tolerance.

sILT3 signaling in T lymphocytes via its ligand may interfere with the generation of effective immunity, promoting the generation of T cells with suppressive function. Because sILT3 has no effect on resting, non-stimulated T cells it is likely to inhibit allograft rejection mediated by T cells activated via direct or indirect pathways. Administration of sILT3 can also attenuate the proliferation of T cells involved in aggressive autoimmune responses triggered by activated DC which cross present immunogenic self-peptides. Attenuation of activation efficiency may result in stalled immune responses which perpetuate quiescence.

These findings have important clinical implications because they open two new avenues for antigen-specific suppression of the immune response in transplantation and autoimmune diseases.

The first avenue resides in treating transplant recipients at the time of or after transplantation or at the onset of an acute rejection episode with sILT3. This molecule is expected to bind only to T cells that have been activated by the transplant's alloantigens and not to unprimed T cells, thus suppressing the immune response in an antigen-specific manner. Similarly, sILT3 administration during the flare-up of an autoimmune attack, e.g., in rheumatoid arthritis, Crohn disease, multiple sclerosis, or onset of type I JDM, may prevent the evolution, e.g., progression of the disease.

The second avenue is to use cell therapy, by leukophoresing the patient and exposing the harvested cells to sILT3 for 18 h. In vitro activated T cells, but not unprimed T cells, are expected to be converted into regulatory cells which, when reinfused into the patient, should block the progression of the immune response.

References
1. "Leukocyte Immunoglobulin-like Receptor, Subfamily B, Member 4; LILRB4," OMIM 604821 (2000).
2. M. Colonna, et al., U.S. Patent Publication No. 20030165875, published Sep. 4, 2003.
3. B. G. Beinhauer, et al., "Interleukin 10 regulates cell surface and soluble LIR-2 (CD85d) expression on dendritic cells resulting in T cell hyporesponsiveness in vitro", Eur. J. Immunol. 34:74-80 (2004).

What is claimed is:

1. A method comprising
   1. identifying a subject that has received an organ transplant, and
   2. administering to the subject an immunosuppressive amount of a soluble polypeptide comprising the extracellular domain of human ILT3.

2. The method of claim 1 wherein the subject has been diagnosed with transplant rejection.

3. The method of claim 1, wherein the soluble polypeptide is operably affixed to the Fc portion of an immunoglobulin.

4. The method according to claim 3, wherein said Fc portion comprises a function-enhancing mutation, wherein the mutation inhibits the binding of said Fc portion to an Fc receptor.

* * *

UNITED STATES PATENT AND TRADEMARK OFFICE
CERTIFICATE OF CORRECTION

| | | |
|---|---|---|
| PATENT NO. | : 8,207,110 B2 | |
| APPLICATION NO. | : 11/661877 | |
| DATED | : June 26, 2012 | |
| INVENTOR(S) | : Suciu-Foca et al. | |

It is certified that error appears in the above-identified patent and that said Letters Patent is hereby corrected as shown below:

On column one, lines 25-28 replace text with the following.

This invention was made with government support under Grant No. AI2521-18 and AI55234-02 awarded by The National Institutes of Health. The government has certain rights in the invention.

Signed and Sealed this
Eighth Day of January, 2013

David J. Kappos
*Director of the United States Patent and Trademark Office*

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatgatatc aggagacgcc atgatcccca                                          30

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgtagcggc cgcgtttct ccctggacgt ca                                        32
```